US010265347B2

(12) United States Patent
Miura

(10) Patent No.: US 10,265,347 B2
(45) Date of Patent: Apr. 23, 2019

(54) BIOMOLECULAR GROUP RELATED TO CELL ANTI-AGING

(71) Applicant: Norimasa Miura, Yonago (JP)

(72) Inventor: Norimasa Miura, Yonago (JP)

(73) Assignee: Norimasa Miura, Yonago-shi (JP)

( * ) Notice: Subject to any disclaimer, the term of this patent is extended or adjusted under 35 U.S.C. 154(b) by 126 days.

(21) Appl. No.: 14/914,788

(22) PCT Filed: Aug. 28, 2014

(86) PCT No.: PCT/JP2014/072661
§ 371 (c)(1),
(2) Date: Feb. 26, 2016

(87) PCT Pub. No.: WO2015/030149
PCT Pub. Date: Mar. 5, 2015

(65) Prior Publication Data

US 2016/0199419 A1 Jul. 14, 2016

(30) Foreign Application Priority Data

Aug. 29, 2013 (JP) ................................ 2013-177763

(51) Int. Cl.
*A61K 35/545* (2015.01)
*C12N 5/074* (2010.01)
*C12N 15/113* (2010.01)
*A61K 35/00* (2006.01)

(52) U.S. Cl.
CPC .......... *A61K 35/545* (2013.01); *C12N 5/0607* (2013.01); *C12N 15/113* (2013.01); *A61K 35/00* (2013.01); *C12N 2310/14* (2013.01); *C12N 2310/531* (2013.01); *C12N 2501/60* (2013.01); *C12N 2501/998* (2013.01); *C12N 2501/999* (2013.01)

(58) Field of Classification Search
CPC combination set(s) only.
See application file for complete search history.

(56) References Cited

U.S. PATENT DOCUMENTS

2009/0047263 A1 2/2009 Yamanaka et al.
2009/0068742 A1 3/2009 Yamanaka
2009/0124794 A1 5/2009 Miura
2009/0131356 A1 5/2009 Bader et al.
2009/0163435 A1 6/2009 Bader et al.
2009/0227032 A1 9/2009 Yamanaka et al.
2009/0232893 A1 9/2009 Bader et al.
2009/0246875 A1 10/2009 Yamanaka et al.
2010/0062533 A1 3/2010 Yamanaka
2010/0075421 A1 3/2010 Yamanaka et al.
2010/0184208 A1 7/2010 Miura
2010/0184216 A1 7/2010 Miura
2010/0210014 A1 8/2010 Yamanaka
2010/0216236 A1 8/2010 Yamanaka
2010/0248356 A1 9/2010 Miura
2010/0285001 A1 11/2010 Land et al.
2011/0070647 A1 3/2011 Dezawa et al.
2012/0082659 A1 4/2012 Land et al.
2012/0114670 A1 5/2012 Land et al.
2012/0244129 A1 9/2012 Dezawa et al.
2013/0052169 A1 2/2013 Marom
2013/0059386 A1 3/2013 Yamanaka et al.
2013/0102768 A1 4/2013 Yamanaka et al.
2013/0184223 A1 7/2013 Land et al.
2013/0184335 A1 7/2013 Miura
2013/0190389 A1 7/2013 Miura

FOREIGN PATENT DOCUMENTS

JP 2010-504350 A 2/2010
JP 2012-085645 A 5/2012
JP 5185443 B2 4/2013
JP 2013-528368 A 7/2013
WO WO-2007/069666 A1 6/2007
WO WO-2009/045443 A2 4/2009
WO WO-2009/075119 A1 6/2009
WO WO-2011/007900 A1 1/2011
WO WO-2011/146879 A2 11/2011
WO WO-2012/008301 A1 1/2012
WO WO-2012/008302 A1 1/2012
WO WO-2014/097875 A1 6/2014

OTHER PUBLICATIONS

Jackson, et al. "Recognizing and avoiding siRNA off-target effects for target identification and therapeutic application." Nature Reviews Drug Discovery, v.9:57. (Year: 2010).*
Zhao, et al. (2008) "Two Supporting Factors Greatly Improve the Efficiency of Human iPSC Generation," Cell Stem Cell, v.3(6):475-9. (Year: 2008).*
Kuroda, et al. (2010) "Unique multipotent cells in adult human mesenchymal cell populations." PNAS, v.107(19):8639-43. (Year: 2010).*
Anokye-Danso et al., "How microRNAs facilitate reprogramming to pluripotency," J Cell Sci. 125(Pt 18):4179-87 (2012).
Extended European Search Report for European Patent Application No. 14840797.6, dated Jan. 18, 2017, Miura, "Biomolecular Group Related to Cell Anti-aging," filed Aug. 28, 2014 (7 pages).
Bradley, "Embryonic stem cells: proliferation and differentiation," Curr Opin Cell Biol. 2(6):1013-7 (1990).
Hasegawa, "Aesthetic Dermatology's Frontline," Visual Dermatology. 12(6):592-7 (2013) (9 pages).
Hong et al., "Suppression of induced pluripotent stem cell generation by the p53-p21 pathway," Nature. 460(7259):1132-5 (2009) (13 pages).

(Continued)

*Primary Examiner* — Jennifer Pitrak McDonald
(74) *Attorney, Agent, or Firm* — Clark & Elbing LLP; Susan M. Michaud

(57) ABSTRACT

Disclosed is a novel process for producing a Muse cell-like cell or a novel method for extending the replicative life span of a cell population. Provided is a process for producing a Muse cell-like cell, comprising the step of inhibiting the expression or function of ELAVL2, TEAD1, or GATAD2B. At this time, siRNA or shRNA may be used to inhibit the expression or function of ELAVL2, TEAD1, or GATAD2B.

8 Claims, 11 Drawing Sheets

Specification includes a Sequence Listing.

(56) References Cited

OTHER PUBLICATIONS

International Search Report for International Application No. PCT/JP2014/072661, dated Dec. 2, 2014 (8 pages).
Knight et al., "TEAD1 and c-Cbl are novel prostate basal cell markers that correlate with poor clinical outcome in prostate cancer," Br J Cancer. 99(11):1849-58 (2008).
Tsuno et al., "Hsa-miR-520d induces hepatoma cells to form normal liver tissues via a stemness-mediated process," Sci Rep. 4:3852 (2014) (14 pages).
Wiszniak et al., "HuB (elavl2) mRNA is restricted to the germ cells by post-transcriptional mechanisms including stabilisation of the message by DAZL," PLoS One. 6(6):e20773 (2011) (9 pages).
Written Opinion for International Application No. PCT/JP2014/072661, dated Dec. 2, 2014 (18 pages).

* cited by examiner

NHDF-Ad

SEQUENCE LISTING

<160> NUMBER OF SEQ ID NOS: 32

<210> SEQ ID NO 1
<211> LENGTH: 21
<212> TYPE: RNA
<213> ORGANISM: Artificial Sequence
<220> FEATURE:
<223> OTHER INFORMATION: small RNA

<400> SEQUENCE: 1
uuauuggugu uaaagucacg g 21

<210> SEQ ID NO 2
<211> LENGTH: 21
<212> TYPE: RNA
<213> ORGANISM: Artificial Sequence
<220> FEATURE:
<223> OTHER INFORMATION: small RNA

<400> SEQUENCE: 2
aauacgagaa guaauaaugc g 21

<210> SEQ ID NO 3
<211> LENGTH: 19
<212> TYPE: RNA
<213> ORGANISM: Artificial Sequence
<220> FEATURE:
<223> OTHER INFORMATION: small RNA

<400> SEQUENCE: 3
uuuguuuguc uuaaaggag 19

<210> SEQ ID NO 4
<211> LENGTH: 21
<212> TYPE: RNA
<213> ORGANISM: Artificial Sequence
<220> FEATURE:
<223> OTHER INFORMATION: small RNA

<400> SEQUENCE: 4
auuugcaucu cugauagaag c 21

<210> SEQ ID NO 5
<211> LENGTH: 48
<212> TYPE: RNA
<213> ORGANISM: Artificial Sequence
<220> FEATURE:
<223> OTHER INFORMATION: small RNA

<400> SEQUENCE: 5
ccgugacuuu aacaccaaua acucgaguua uugguguuaa agucacgg 48

<210> SEQ ID NO 6
<211> LENGTH: 48
<212> TYPE: RNA
<213> ORGANISM: Artificial Sequence
<220> FEATURE:
<223> OTHER INFORMATION: small RNA

<400> SEQUENCE: 6
cgcauuauua cuucucguau ucucgagaau acgagaagua auaaugcg 48

<210> SEQ ID NO 7
<211> LENGTH: 46
<212> TYPE: RNA
<213> ORGANISM: Artificial Sequence
<220> FEATURE:
<223> OTHER INFORMATION: small RNA

<400> SEQUENCE: 7
cuccuuuaag acaaacaaac ucgaguuugu uugucuuaaa ggagac 46

<210> SEQ ID NO 8
<211> LENGTH: 48
<212> TYPE: RNA
<213> ORGANISM: Artificial Sequence
<220> FEATURE:
<223> OTHER INFORMATION: small RNA

<400> SEQUENCE: 8
gcuucuauca gagaugcaaa ucucgagauu ugcaucucug auagaagc 48

<210> SEQ ID NO 9
<211> LENGTH: 19
<212> TYPE: RNA
<213> ORGANISM: Artificial Sequence
<220> FEATURE:
<223> OTHER INFORMATION: small RNA

<400> SEQUENCE: 9
uuggcuuauc ugcagaguc 19

<210> SEQ ID NO 10
<211> LENGTH: 18
<212> TYPE: RNA
<213> ORGANISM: Artificial Sequence
<220> FEATURE:
<223> OTHER INFORMATION: small RNA

<400> SEQUENCE: 10
gcuuguuaug aauggcag 18

<210> SEQ ID NO 11
<211> LENGTH: 19
<212> TYPE: RNA
<213> ORGANISM: Artificial Sequence
<220> FEATURE:
<223> OTHER INFORMATION: small RNA

<400> SEQUENCE: 11
guaagaaugg uuggcaugc 19

<210> SEQ ID NO 12
<211> LENGTH: 19
<212> TYPE: RNA
<213> ORGANISM: Artificial Sequence
<220> FEATURE:
<223> OTHER INFORMATION: small RNA

<400> SEQUENCE: 12
aguuccuuua agccaccuu 19

<210> SEQ ID NO 13
<211> LENGTH: 46
<212> TYPE: RNA
<213> ORGANISM: Artificial Sequence
<220> FEATURE:
<223> OTHER INFORMATION: small RNA

<400> SEQUENCE: 13
gacucugcag auaagccaac ucuugauugg cuuaucugca gagucc 46

<210> SEQ ID NO 14
<211> LENGTH: 45
<212> TYPE: RNA
<213> ORGANISM: Artificial Sequence
<220> FEATURE:
<223> OTHER INFORMATION: small RNA

<400> SEQUENCE: 14
cugccauuca uaacaagccu cuugagcuug uuaugaaugg caguc 45

<210> SEQ ID NO 15
<211> LENGTH: 46
<212> TYPE: RNA
<213> ORGANISM: Artificial Sequence
<220> FEATURE:
<223> OTHER INFORMATION: small RNA

<400> SEQUENCE: 15
gcaugccaac cauucuuacc ucuugaguaa gaaugguugg caugcc 46

<210> SEQ ID NO 16
<211> LENGTH: 46
<212> TYPE: RNA
<213> ORGANISM: Artificial Sequence
<220> FEATURE:
<223> OTHER INFORMATION: small RNA

<400> SEQUENCE: 16
aagguggcuu aaaggaacuc ucuugaaguu ccuuuaagcc accuuc 46

<210> SEQ ID NO 17
<211> LENGTH: 19
<212> TYPE: RNA
<213> ORGANISM: Artificial Sequence
<220> FEATURE:
<223> OTHER INFORMATION: small RNA

<400> SEQUENCE: 17
caacagauuc aagcgaaga 19

<210> SEQ ID NO 18
<211> LENGTH: 19
<212> TYPE: RNA
<213> ORGANISM: Artificial Sequence
<220> FEATURE:
<223> OTHER INFORMATION: small RNA

<400> SEQUENCE: 18
caauagaugc ugcauucug 19

<210> SEQ ID NO 19
<211> LENGTH: 19
<212> TYPE: RNA
<213> ORGANISM: Artificial Sequence
<220> FEATURE:
<223> OTHER INFORMATION: small RNA

<400> SEQUENCE: 19
caucaacaug uguggaagg 19

<210> SEQ ID NO 20
<211> LENGTH: 19
<212> TYPE: RNA
<213> ORGANISM: Artificial Sequence
<220> FEATURE:
<223> OTHER INFORMATION: small RNA

<400> SEQUENCE: 20
aggauguugu acgcugaca 19

<210> SEQ ID NO 21
<211> LENGTH: 45
<212> TYPE: RNA
<213> ORGANISM: Artificial Sequence
<220> FEATURE:
<223> OTHER INFORMATION: small RNA

<400> SEQUENCE: 21
ucuucgcuug aaucuguugc ucuugacaac agauucaagc gaaga 45

<210> SEQ ID NO 22
<211> LENGTH: 46
<212> TYPE: RNA
<213> ORGANISM: Artificial Sequence
<220> FEATURE:
<223> OTHER INFORMATION: small RNA

<400> SEQUENCE: 22
cagaaugcag caucuauugc ucuugacaau agaugcugca uucugc 46

<210> SEQ ID NO 23
<211> LENGTH: 46
<212> TYPE: RNA
<213> ORGANISM: Artificial Sequence
<220> FEATURE:
<223> OTHER INFORMATION: small RNA

<400> SEQUENCE: 23
ccuuccacac auguugaugc ucuugacauc aacaugugug gaaggc 46

<210> SEQ ID NO 24
<211> LENGTH: 46
<212> TYPE: RNA
<213> ORGANISM: Artificial Sequence
<220> FEATURE:
<223> OTHER INFORMATION: small RNA

<400> SEQUENCE: 24
ugucagcgua caacauccuc ucuugaagga uguuguacgc ugacac 46

<210> SEQ ID NO 25
<211> LENGTH: 689
<212> TYPE: DNA
<213> ORGANISM: Artificial Sequence
<220> FEATURE:
<223> OTHER INFORMATION: vector

<400> SEQUENCE: 25
ggaaccaacc ccccttcgag ccgcggccaa agtggatctc tgctggtccc tgtaataaac 60
ccgaaaattt tgaatttttg taatttgttt ttgtaattct ttagtttgta tgtctgttgc 120
tattatgtct actattcttt cccctgcact gtacccccca atcccccctt ttcttttaaa 180
attgtggatg aatactgcca tttgtctcga ggtcgagaat taaaaaccgt gactttaaca 240
ccaataactc gagttattgg tgttaaagtc acggccggtg tttcgtcctt tccacaagat 300
atataaagcc aagaaatcga aatactttca agttacggta agcatatgat agtccatttt 360
aaaacataat tttaaaactg caaactaccc aagaaattat tactttctac gtcacgtatt 420
ttgtactaat atctttgtgt ttacagtcaa attaattcca attatctctc taacagcctt 480
gtatcgtata tgcaaatatg aaggaatcat gggaaatagg ccctcggtga agggggcggc 540

```
cgctcgaggc ttagtctcgt gatcgatacc gtcgagatcc gttcactaat cgaatggatc    600

tgtctctgtc tctctctcca ccttcttctt tctattcctt cgggcctgtc aggttccccc    660

tcgggggttg ggaagtgggg tctgaataa                                      689


<210> SEQ ID NO 26
<211> LENGTH: 913
<212> TYPE: DNA
<213> ORGANISM: Artificial Sequence
<220> FEATURE:
<223> OTHER INFORMATION: vector

<400> SEQUENCE: 26

ggcccaatcc ccttcgagcc gcggccaagt ggatctctgc tgtccctgta ataaacccga     60

aaattttgaa tttttgtaat ttgtttttgt aattctttag tttgtatgtc tgttgctatt    120

atgtctacta ttctttcccc tgcactgtac cccccaatcc cccctttttct tttaaaattg    180

tggatgaata ctgccatttg tctcgaggtc gagaattaaa aacgcattat tacttctcgt    240

attctcgaga atacgagaag taataatgcg ccggtgtttc gtcctttcca caagatatat    300

aaagccaaga aatcgaaata ctttcaagtt acggtaagca tatgatagtc cattttaaaa    360

cataatttta aaactgcaaa ctacccaaga aattattact ttctacgtca cgtattttgt    420

actaatatct ttgtgtttac agtcaaatta attccaatta tctctctaac agccttgtat    480

cgtatatgca aatatgaagg aatcatggga aataggccct cggtgaaggg ggcggccgct    540

cgaggctagt ctcgtgatcg ataccgtcga gatccgttca ctaatcgaat ggatctgtct    600

ctgtctctct ctccaccttc ttcttctatt ccttcgggcc tgtcgggtcc cctcggggtt    660

gggaggtggg tctgaaacga taatggtgaa tatccctgcc taactctatt cactatagaa    720

agtacagcaa aaactattct taaacctacc aagcctccta ctatcattat gaataatttt    780

atataccaca gcccaatttg ttatgttaaa ccaattccac aaacttgccc atttatctaa    840

ttccataatt cttgttcatt cttttcttgc tggtttgcga ttcttcaata gagtgtatta    900

gcttgtgtat gta                                                       913


<210> SEQ ID NO 27
<211> LENGTH: 962
<212> TYPE: DNA
<213> ORGANISM: Artificial Sequence
<220> FEATURE:
<223> OTHER INFORMATION: vector

<400> SEQUENCE: 27

ggccccaccc ctcgagccgc ggccaagtgg atctctgctg tccctgtaat aaacccgaaa     60

atttttgaat ttttgtaatt tgtttttgta attctttagt ttgtatgtct gttgctatta    120

tgtctactat tctttcccct gcactgtacc ccccaatccc cccttttctt ttaaaattgt    180

ggatgaatac tgccatttgt ctcgaggtcg agaattaaaa agtctccttt aagacaaaca    240

aactcgagtt tgtttgtctt aaaggagacc cggtgtttcg tcctttccac aagatatata    300

aagccaagaa atcgaaatac tttcaagtta cggtaagcat atgatagtcc attttaaaac    360

ataattttaa aactgcaaac tacccaagaa attattactt tctacgtcac gtattttgta    420

ctaatatctt tgtgtttaca gtcaaattaa ttccaattat ctctctaaca gccttgtatc    480

gtatatgcaa atatgaagga atcatgggaa ataggccctc ggtgaagggg gcggccgctc    540

gaggctagtc tcgtgatcga taccgtcgag atccgttcac taatcgaatg gatctgtctc    600

tgtctctctc tccaccttct tcttctattc cttcgggcct gtcgggtccc ctcggggttg    660
```

ggaggtgggt ctgaaacgat aatggtgaat atccctgcct aactctattc actatagaaa 720
gtacagcaaa aactattctt aaacctacca agcctcctac tatcattatg aataatttta 780
tataccacag ccaatttgtt atgttaaacc aattccacaa acttgcccat ttatctaatt 840
ccatattctt gttcattctt ttcttgctgg gtttgcgatt cttcattagg agtgtattaa 900
gctgtgtatg taattctctg tcccactcca atccagttcg tgatgattcc caaatcctgg 960
gt 962

<210> SEQ ID NO 28
<211> LENGTH: 966
<212> TYPE: DNA
<213> ORGANISM: Artificial Sequence
<220> FEATURE:
<223> OTHER INFORMATION: vector

<400> SEQUENCE: 28
ggacccaacc cccttcgagc cgcggccaag tggatctctg ctgtccctgt aataaacccg 60
aaaattttga atttttgtaa tttgtttttg taattcttta gtttgtatgt ctgttgctat 120
tatgtctact attctttccc ctgcactgta ccccccaatc cccccttttc ttttaaaatt 180
gtggatgaat actgccattt gtctcgaggt cgagaattaa aaagcttcta tcagagatgc 240
aaatctcgag atttgcatct ctgatagaag cccggtgttt cgtcctttcc acaagatata 300
taaagccaag aaatcgaaat actttcaagt tacggtaagc atatgatagt ccattttaaa 360
acataatttt aaaactgcaa actacccaag aaattattac tttctacgtc acgtattttg 420
tactaatatc tttgtgttta cagtcaaatt aattccaatt atctctctaa cagccttgta 480
tcgtatatgc aaatatgaag gaatcatggg aaataggccc tcggtgaagg gggcggccgc 540
tcgaggctag tctcgtgatc gataccgtcg agatccgttc actaatcgaa tggatctgtc 600
tctgtctctc tctccacctt cttcttctat tccttcgggc ctgtcgggtc ccctcggggt 660
tgggaggtgg gtctgaaacg ataatggtga atatccctgc ctaactctat tcactataga 720
aagtacagca aaaactattc ttaaacctac caagcctcct actatcatta tgaataattt 780
tatataccac agcccaattt gttatgttaa accaattcca caaacttgcc catttatcta 840
attccataat tcttgttcat tcttttcttg ctgggtttgc gatcttcatt taagagtgta 900
ttagccttgt gtatgttatt tctctgatcc atcatccagg tcggtgtgta ttccaaaacc 960
tcccct 966

<210> SEQ ID NO 29
<211> LENGTH: 3780
<212> TYPE: RNA
<213> ORGANISM: Homo sapiens

<400> SEQUENCE: 29
agcgaguccg aacucugggc gggaacacug gugggggcgg cggagguugu gcccgcgaag 60
uuccuagagc ucagcccguu gcggcgggag uagagagaau ugggcgccuc gggagguggc 120
accgccccuc ccgugggcac aagcagguug ggggcggcgg gagccgagcg gggacagucg 180
cgccuggcag cgugcacggg cguggacgug cccgggugcg gccgcgugua gcgcaagaag 240
gaaacuguug agacgcagca gguaauugcu gccauggaaa cacaacuguc uaaugggcca 300
acuugcaaua acacagccaa ugguccaacc accauaaaca acaacuguuc gucaccaguu 360
gacucuggga acacagaaga cagcaagacc aacuuaauag ucaacuaccu uccucagaac 420
augacacagg aggaacuaaa gagucucuuu gggagcauug gugaaauaga guccuguaag 480

-continued

```
cuuguaagag acaaaauaac agggcagagc uugggauaug gcuuugugaa cuacauugac    540
cccaaggaug cagagaaagc uaucaacacc cugaauggau ugagacuuca aaccaaaaca    600
auaaaaguuu ccuaugcucg cccaaguuca gcuucuauca gagaugcaaa uuuauauguc    660
agcggacuuc caaaaacaau gacccagaag gaguuggaac agcuuuuuuc acaauaugga    720
cgcauuauua cuucucguau ucuugucgac caggucacug gcauaucaag ggguguaggg    780
uuuauucgau uugacaagcg aauugaggca gaagaagcua ucaaaggccu aaauggccag    840
aaaccucccg gugccacgga gccaaucacu guaaaguuug cuaauaaccc aagccaaaaa    900
accaaucagg ccauccuuuc ccagcuguac cagucuccaa acagaaggua uccaggaccg    960
cuagcucagc aggcacagcg uuuuagguuu ucuccaauga ccauugacgg aaugaccagu   1020
uuggcuggaa uuaauauccc ugggcacccu ggaacagggu gguguauauu uguguacaac   1080
cuggcuccug acgcagauga gaguauccug uggcaaaugu uugggccuuu uggagcuguc   1140
accaauguga aggucauccg ugacuuuaac accaauaaau gcaaagguuu uggauuugug   1200
acuaugacaa acuaugauga ggcugccaug gcgauagcua gccucaaugg auaccgucug   1260
ggagacagag uacugcaggu cuccuuuaag acaaacaaaa cgcacaaagc cuaaugagcu   1320
cuuguccuca guccauuuau auaugaaaac uauacaacaa aggcaaguua agagaaacuu   1380
uauacauuag uaaaugucuu uguaagucag uguugagaug ggauaaaaau gacuacuuag   1440
cauccuaaga aauaugugag auuuuuuauu gcuaguauuu gaauuaaaac uucuuaaaua   1500
ucuuuuaugu uugaauaugg acaagaggua caggguuuuu accugucaca uugcauucua   1560
uugccuucuu ugaagaaggu ggaccuuuua aaguguuuca gcuaagggaa gacauuucuu   1620
uucuuuuuac auaacugccu ugaaccugug aguaaauauu gaggcuuugu guuguaauuc   1680
uucaguuggu ugugucuuuu uuuuccccc uuuuuuuccu uuuucugauu agcuuugugu    1740
uugguuuaca uuuaaagcau ugcuguuaug ucuguuuaag aaaaguauuu ugaaguuuac   1800
auuuuuauuu augaaguuua aaacaguauu uauuuuguaa uuaugauuug gguuggggaa   1860
ggggggggcua cauuauaaac gcuuauugua agaauacugg agaacuuuuc guaaagcagu   1920
accuugccaa agagauaaga gccucuuuga ugugggguua aaaaaagcau cuauuuuuau   1980
aaaaaagaaa auuuggagaa acuuuuuacu gguccuggaa caaauauuuu gacuugaaua   2040
cuuugagaaa ucucuucaua ugacaccuag ugagcuuuua aaauuuacca ggaaauuugc   2100
agcgguugga aaauuuagaa agauuuaugg uguagaaaau acuuuugaga ucuuuguaug   2160
aaaggaguag aaucaauggg gggaaacacu gcugguuuca uuuuuguaau caccagugga   2220
gcgucugauc auccugguua uuaugugaua gguggcucac auugauuugu gauuuugaaa   2280
caaauaaaaa aaauuuacaa aagaauauau aagagcaggc aagaaauuua aauuaccgag   2340
agaugggggga aaaaaucugu ucuuccuaaa gaaaucccuu cagauagagc ucaugguguu   2400
uagugaugua cuugcaguau uguuugaaga auuguuuugu cuuaaggaaa aaagacguug   2460
cacaugauuu guacugcagc aaaucagcaa aagugaucug aguuggauau auuugaaggu   2520
auuuugaaag uuacguucaa ggcuaacacc ugagcuuugu guaauguaaa uaagaccuug   2580
uguuuaugaa ccuuucagcu aauuuaauuu uuuuucccuu acaugccaag ugauguucag   2640
guuuugaaug uuuuuguauc aguuuuuucc uuuguaaaug gcauuaacau uguuacuuga   2700
ggucuugcuu aaucacuuuu guuguccuga ggacuugaau uuacagugca ucagauuugu   2760
ugcaaauuuu gucuguagau agucuagcuu cagcuguuua uggugaugcu acauuuucgu   2820
uuauaaauau guuuguggua uaaaaaaaug aguauaacca uagguuuuga acaaauuucc   2880
```

```
uuacauuuuu cauacaaaaa ucauaaaauau cuguaugcua uugaaauuua acuuuguaug   2940

augcuuaaaa accacuauuu ggggaaauaa uaaaauaagu cuuuaccaug uaugaaagaa   3000

auuuuaaaaa auacaaaaua uuuucugauu agcaucuagc uuauaauaaa uuuucaaaaa   3060

agcugaaggc aaaaaugccu ucaucaggau gcacugagaa cuauauaguu acguccugcu   3120

uuuuguauaa acugagaugc ucacaugcuu ccccuuagaa caggcaaugu gcuaugcaua   3180

acauaguugu acauuaucuu ugcgguugcu uugaguuuua uuuuuuauua uuuaaaauug   3240

uaguuauaaa auuuuucagu auaguacagu acauauacug ugaggcgcgu gcuaaaguga   3300

auaagcgagu uuucaugcug acccacucaa ugcuauucag aaaucaauug gcuuagcacu   3360

uucucauauc cuuaggugca uuuagauugc cagaguuaac cuucugcguu uaaaaaaaga   3420

aaaacacuaa aaaauaaaau acauguauau acuuaaaaaa aaauaauaag guuucccuca   3480

agggaaaaca gcagcuacau gcuucuuucc uauacuacug uagcaaacca aggcauugau   3540

gagagggcau gcaaauugug cuucacuuua caguguuuua ucagagcacu uaauaaaaug   3600

uaaggcuggu auuuauuuga aguuguacag uaugacuuaa uucacaucug uuggaauaga   3660

aaauauauuc uguugaguau uuaagaggcu guacauguuu ucuuuugugu uuggauucuu   3720

uguacuuuuu cauguucagu acaucaauaa acaaaguuga agggaaaaaa aaaaaaaaaa   3780
```

<210> SEQ ID NO 30
<211> LENGTH: 9433
<212> TYPE: RNA
<213> ORGANISM: Homo sapiens

<400> SEQUENCE: 30

```
uuccgaacau ucuuagcauc gcucgcgccg cgccgcgccg ccugagccga gccgagccuc     60

ugcugccgcc gccgcggccc cgccgcccgc cgcgggcgcc caccaagcac uuugcagacu    120

cgcuuccacc cugcgggcca uuccgcgcgg cggggcccgg gcccggggcg gccgcgucca    180

ggcacaggcc augcagugac gccccccccac cccuccaccu uugcccggag cgcgggcagc    240

agcccagcgc gccagccggc cccggggcag gagcggugcu aggcaggggu gggguggccg    300

ggcccaggga ccgggagccg gggagggagc cgggcaccga gcagagggcg ggggaagcgg    360

cgccgaaguu ugccucggac ucgccgggcg cugcgguggc ucccugggcc gaggacuguu    420

gcugccgcug ccgccgccgc uucauugcac auucaagugg aaaauuuuca ggagucagca    480

gaaacauugu guccaaaaaa gacugagucg caguuaccac caaacccagg aggagacucu    540

cccuggaaaa cuucccuucc cuuucgguuu auuuucuuga aaaggcucca ggcuucggcu    600

uggaaaaucc caccgccaaa auugagccca gcagcuggag cggcagugag agcccugccg    660

aaaacaugga aaggaugagu gacucugcag auaagccaau ugacaaugau gcagaagggg    720

ucuggagccc cgacaucgag caaagcuuuc aggaggcccu ggcuaucuau ccaccaugug    780

ggaggaggaa aaucaucuua ucagacgaag gcaaaaugua ugguaggaau gaauugauag    840

ccagauacau caaacucagg acaggcaaga cgaggaccag aaaacaggug ucuagucaca    900

uucagguucu ugccagaagg aaaucucgug auuuucauuc caagcuaaag gaucagacug    960

caaaggauaa ggcccugcag cacauggcgg ccauguccuc agcccagauc gucucggcca   1020

cugccauuca uaacaagcug gggcugccug ggauuccacg cccgaccuuc ccaggggcgc   1080

cgggguucug gccgggaaug auucaaacag ggcagccagg auccucacaa gacgucaagc   1140

cuuuugugca gcaggccuac cccauccagc cagcggucac agcccccauu ccaggguuug   1200

agccugcauc ggccccagcu cccucagucc cugccuggca aggucgcucc auuggcacaa   1260
```

-continued ccaagcuucg ccugguggaa uuuucagcuu uucucgagca gcagcgagac ccagacucgu 1320
acaacaaaca ccucuucgug cacauugggc augccaacca uucuuacagu gacccauugc 1380
uugaaucagu ggacauucgu cagauuuaug acaaauuucc ugaaaagaaa gguggcuuaa 1440
aggaacuguu uggaaagggc ccucaaaaug ccuucuuccu cguaaaauuc ugggcugauu 1500
uaaacugcaa uauucaagau gaugcugggg cuuuuuaugg uguaaccagu caguacgaga 1560
guucugaaaa uaugacaguc accuguucca ccaaaguuug cuccuuuggg aagcaaguag 1620
uagaaaaagu agagacggag uaugcaaggu uugagaaugg ccgauuugua uaccgaauaa 1680
accgcucccc aaugugugaa uauaugauca acuucaucca caagcucaaa cacuuaccag 1740
agaaauauau gaugaacagu guuuuggaaa acuucacaau uuuauuggug guaacaaaca 1800
gggauacaca agaaacucua cucugcaugg ccugugugu ugaaguuuca aauagugaac 1860
acggagcaca acaucauauu uacaggcuug uaaaggacug aacaugguua uuuauauaua 1920
uagauaucug uauauacaca cacacauaug ugcacacaca cacucucucu ccauuaucga 1980
acgacugacu guaaaccuca ccacacaggg uggugcccug gccccgaggu caccccgacu 2040
uuucuaaauc uuguuugagu gaagucauuu uuucaugugu ucauacuauc auuguagcug 2100
ugaaguucug guacaguugu aaaaagagaa auugaguugu uucucuaugu ucuucagaug 2160
ugcagcccac aauuccucgg gaaaggugaa ccugaacaac ccaagucucu cucugcagag 2220
cccuguuucu aauuguggua gaaaauauug agacagagca uuugccaugg gacauuuaca 2280
gccuuuauac aaauguauuu aguucucuuu uuuccaacau aaaauucuug uuuuaagaua 2340
caaguaaaau uaaucuuuaa auauaaaugu aaauuaguac acaaaacuaa gaaucuuuag 2400
acuuaucuuu guaacuaauu agggguggaag uuaugaaaga auguaauuca cuaaauuauu 2460
uuuuaaauga aaccuuuuuu uuucuuuuug aaaccaaaug uuaaacuaua gccuuaagaa 2520
augcuuggua gaaguguccu aaugagacaa auuuguacuu uuauccucaa gguuaacacu 2580
aaucuccuaa uccauuaaac ucuugaacag guauuacaaa ggaagaaaac uucaccccuu 2640
auccuuaaca uauauaguau auuuaaaaaa uauaaaauug uauuguacua augugaugau 2700
ggauuauuua augaaaaaga aaaaauggcu cuuuuugcaa uaaguagaua cauacugaaa 2760
aaaucuaaac uuacaauguu uauagucuug ugugugcagu uauauuuuau auggacgacc 2820
aaauuuuuua uuaagaugag uaaauauuug aaccacugaa uuuuaauaac aaaauuuuaa 2880
aauuggcaug aauacggaau acugcacugu gagaugcaaa guauacagaa ucuguggcug 2940
ggagaaaauu ucaucaaaua gacaaguaaa aggcucauca guuuuagcau cucugcuccc 3000
cagaaaauug uaagcauccu caccagccug uggauacauu cuuuauuucu agugacccaa 3060
uaugcauauu aaccugcuau aacuagggcu auauguguag guauguguau acauauacac 3120
aaaugcacau auagaguuaa cacauuuagu gaacacuugu uuagugucac ucaguuugcu 3180
aggugcugau auguacguau aucucaaugu gucuguagac uuagauacau ccucuugaag 3240
cacauccauu ucuuuagcgu cucucaguaa guuacaguac uuguuugacu uagguuuaag 3300
aggcccagcu accuaucucu gaccuuuuca aauaggcuca uuugggagau ucuuuugcca 3360
ggagagauuc aacuuuccaa ucuaaguauu ccagagcauu gcccaggcag aguugguuug 3420
auguggccag auguuuugag uuauuucccu uaaguguuuc acuggggaga gaacagggag 3480
ugcuccucca gcuucccaaa gaaauauguu uuuguaagug guaggaacau gugcacacaa 3540
uagaacauga aauaaguuuu uuaacuugua aaacauguca agauuuuucc accaagcuag 3600
aaaauaaaaa acuuaguucu accacaucca auuaacuuac acaccccccuu cccugucuca 3660

-continued acaccugcuu ugacccugcu uuucuauuau uacaucaguc agcaucuugu ggucccuaac 3720
augaggaugu ggcuggcucg ugggaaacag caaaacacua agccugaccu cucccaaauu 3780
gggaagacca gaggagaaag ugcaaaacug uccccauuug gaaugcccau uccuucuaga 3840
aaccaguugg acagugcucc ucugcccuuc auaaacagac uacuguuggg ucccugauuc 3900
caggcuggcc ugugaaggau ugccccaggu guccccuuuc acgguuguca cauuuacagu 3960
gacuucuguu gaacaccccu cuuagggaug uuucuuuugc ucuuauuucc ugcaucuuuc 4020
cuuaagggaa gccccauccu cucccaggac caggaguuua ugaccaggcg agcacaaaug 4080
gcuaaaagcc aagcuguccu agaacuucag ugggagagcu gucugguuca uauucuaccc 4140
aggaauggua cuuuucagug cagccaggag ggcucuuggg auuuccuuuc caaagcacaa 4200
aaauacuggg acccaagaag aacagcuaga ggacaacucu guuggcacag agacggggac 4260
agcccagucu gcugaccuca cagggucagc ugggcccccc uggugcuuca ccaccugcau 4320
ccucuugcuc agaaugccuu ugcaguugag uuuucugggu uucuaugauu gaccuugagg 4380
uuuacuccuu gcucuuacaa cauuucuaag gauuuuuaaa aguuuacuuc uugucuuguu 4440
cuucuaaagc uuucuccagg acagauauuu ucccugucuu aaccacuggu ccagucaucc 4500 caguggggcuu cucuuugucu cucccagauu agaccuuugg gugagauugg caucacaaca 4560
ucuaaucuga gucugucuuu uguccuucau ucuguauggc agucucccuu uguuauaaaa 4620
gcuuucuaaa gcauacuaaa gaagccuucc cagagccccg ucuugcuucu cuuccaggug 4680
cucuaucccc ucgagacccu cuggugccag gcuugcuuca cggccaucuu guguugucac 4740
ugcagaguuu ggaggccagu uuuccacagc cuaaacaggg aggagcugca gaauggggcu 4800
cuggucucug ggcauucauu ucccucauag aggcugagaa uaaaacaagg acuuauucac 4860
acauguucua gaaccccaga auggcccaag uuaccugaga ccaggguuuc ucaaccuuga 4920
caccauugac auuuuggacu ggguaauucu uuguucugca gagcuguccu uugcacugua 4980
ggagauuuac uaauaucccu ggccucuacc caguaguacc acuagcaccu auuccccacc 5040
cagcgugucu ccagauauug ucaaauaucc caucgggugc aaaaugaucc cuggucaaga 5100
ucuguugccc aagauguuac aggucacaau gaccacauuu gaaauuguuu ucccuuucau 5160
uuuacccugu gaaagcaucu cuccuagagc cuugcaagag gcaggugaca uuguguccau 5220
auuucuuccu guuucagaac uucuguuuca caacaauuuc ucucucgcua caaguauucu 5280
uucacucagc acuggggaag uugggaacag cuggucacca ucaucccuuu aaucaacuca 5340
caccuguuua aagaguguuu cugauuugac cuucaucccu uaguuuacug gcguuaaaaa 5400
aagucucagc aauuuucauu auuucucgug ggucucauua ucaaaccuuu acuuauuucg 5460
gcauauuucc ucugggcuuc uucuaguuuc ugccuuacaa gcaaugcugu ucuguaaauu 5520
uauugaaacc ucuggaacau uucaccuuua gagauggagg auggaaggau ugguaccaga 5580
agagggcuaa gauacguuuu cugucuugag cugaaagcac agucuacucu ccuucguuuu 5640
gucgaugaga aaguugaggc cagaggggag gugacauguu uagagucacc cagcugguua 5700
gugacagaaa aagcgugaga guugucuagg auuccugcca cuuugguccc uggccucucc 5760
ugggggaggc ugcuguucuu aggugcucua agcuuaaucc cucagaaugu guggacaggu 5820
cagcuuagaa gagaugggga gauucaggau cccccugugc cagagcacag ccucaccgga 5880
ugcugcuucc cacacugaag uguccugucc gaccauugcu aucugaggca uccacaagca 5940
gguaggaaag cuggcgagcc auuuuacuuc cugaggacaa uuccccagcc acaggcucug 6000
agucaaauuu cuauuuggua agcauccuag cagcaaaguc cugcacucag accagccaaa 6060

```
aaacagcccc cauuccaagu acuuggugug aaaaguccccc gaacgacuuu uaaacccaag   6120
ucuucuuaag guuucaguac ugugguggcu uuagcaguug uuuuugugca acuauaaauu   6180
auuuaaauca ucugagauga cagucaauuu uacaaaccag guacauauua auuuguauaa   6240
uuuuguauau gcucugguac acuaccugaa cuaacgaagg guagaacuaa uucuguuugu   6300
caguguucac accuguaaca uuaggaggau augucugcau ugcuuauuuc uuuauguugg   6360
uguuucugug gcaaagcccu gcacauggca uuucugaaaa gccuuaaauc uuuaagaugu   6420
ugcauguagg guaugcagug caaaaggcug ccucagaacu gugagcccuu uuguaagcug   6480
gaagcauuuc ucuuacuacu guuacuuuug uaggaaguuu ucaauucaga gcugccaaag   6540
uguucccgua agcagugccu uaguaauacc uuagucaugc cgccagccuu uucuuacacc   6600
aauuccuaau guucauuuac gaauuggccc aauauuggaa acaaaacaag caaaaauugu   6660
cuucauuuuu guuuuguaag cccauuuuuu cuccaguucu auaggaaacu gacugcuugg   6720
uguaaaaucc gaaacuggac acaagucagu ucuuucacca cacucaaaug uauauaccaa   6780
aacaaaaggu ugcaacuuca uaguuuacua ugaaaagcaa auuguacuuu uuaauguugc   6840
cuuuuaaauu caugaccaaa uacuuagcua uuugugaauc uucugcacuc uagcaugaaa   6900
gugccuuugg uuugagauuc cagcuuagaa aagugcugcc auaauaacga uaauuuguag   6960
agagaccaaa aauauuuuga gaucaccgua augccuuugg uuuaccggga ugaguaacca   7020
accacaggcc ucuguucaca agagcacgac gugguccccg ccugcugcua gucugucugc   7080
cacugggggc cucccaacau ccauagcaca cuucagcgga aggaccccag aaacuguugu   7140
guuugugugu gcugaugacc uaguguguca uuucaccucg ucacccagcc cugcguccgg   7200
augaggggac uucugcacaa augacagaau cucggcuggu ggacagauac uacagcuuuc   7260
uccuccuccu uguguucgug uucagucucu guggagacuu ucuuuuccau ucaaaugaca   7320
gugcgcacuu aucugguuua cacaaugaua ccauuuugaa aguuggaagc cucaaacuga   7380
gacgacagug cagaacaaaa caaaagugag uuagggucgu uaaaauugaa guguucuucu   7440
uagggcaaac auguugacuc cgaguauugu guaugaaugu gcuacgagaa acuuccaaag   7500
agcaccauuc acaauuuggc auuuucaaag aauguuccag cccucaaagg ggcaacucuu   7560
uaaaguccuu guuggcuuuu auccaaaccu uguagaaauu gggaaagcug auagagguaa   7620
ggaagacgag ugaaaaggac aagaaggcca aacaccagcc aaaaagaaac uaggaaaaaa   7680
agauuuucuu ugcuaauaua gauguaaaaa uaacaucaga caucuuugaa aauuagccuc   7740
uaaacucuua auacauacgu ucugugugucc ucuaccuggc gucuuuaaga auauccucuc   7800
ugggcucuga aauuuuagga gugauucuua uccacuccaa guuguaagua uuuguagaaa   7860
uuugugcaaa caaacaaaaa cuaucaaaug aaaagaaaau guacucaacc uaacuuauag   7920
uuagcagcug gaauucucaa cucuucccug ccagcacuau accacagugu ggaagaaauu   7980
agucaaaugc uuguuuuccu gcuucucuuu ucaacuguua cugugcuuug uuugaaagua   8040
guuuucucuc ucaaagccgu ugcuuauauc guuaagaaug aagguuugug uuuaaaauuu   8100
auugcauugc aaaggguagu uucacugaag ucaugcacca uuaaauaaga ugaaauauuu   8160
guauuuauug uccuacuucc uaagccguaa cuucuuuucc ucugugaauu ugcauugagu   8220
cacucaugcu acacuacauc gcuuuaguau uugagauggc auuuauguuu ccucucguuu   8280
aucaugaaau ggggucagau uccaucagau uccaccucug ucagguggac ucuugucugc   8340
cuuccaugau gagauuuuuu uucuccuucc ccuuucuuua agagaggcug acagaucuag   8400
gugucaauca auuggaaacc agucucugau uuuuuuucau uaguuauuuu cuaucauuag   8460
```

```
uuucacugug uaaauuagau aucaacugca cuucuuuaaa aaaaaauaca ucucccuauu   8520
accuccuuga aagauuuacu ucuguaggcc uuuuucaaua ggcucaugac ugcagacaag   8580
gaaaaaaaaa guaaaaacaa aaacaguaug ugccugaaaa ugacaaaaaa aaaauuugua   8640
acauuuaaaa aagaaaccug aauagccuuu aauucuuuaa uaauacacuu aaauuuuaug   8700
uaaaucgguu uucgccacgu guguuuguuc acauucuaaa ugacuuaaug ggauucucac   8760
ggucuguguc uuugugucac guguauaaaa ugggcuugug auguaagcgu uucaucuggu   8820
caguggguucc uuugauauug uacugcugcu gggagugggc uguggaaccu gccuucgggu   8880
aacuggguuc cucuugggua gauuggagag augggggugg gcgugggcaa auucucacac   8940
auguuuucuu aaccuauuug cagaaacuuu caaaaggcau uugauuaaac cucuuggcag   9000
uacaguauuc uuguauuugu uaacgucugu guuuagguac ugguaccuuu uuguuuuaaa   9060
auguucuaag uguuggcuuu aaagugaauu uaucuuuagu augauaguua uaugaaaauu   9120
auaggauuug ugugcagaga auuuuuuuau aaagugcuuu guaaaaaaaa aaaaauguau   9180
ucuagcuuuu gcgguacaua ugugugauaa cuuuaauacc caugacaguu aagugcaauu   9240
auuucaucac ucuaaaaaug cuauuuuugu gucaguuccu gcagguguuu ucaugucuuu   9300
gcaaagugac acauuuugau gccuucuuga uaaaguggua gacauuuugu agcuuucuag   9360
aaacuuugua uucauacggu aucaaugaaa aauaaagaaa augaaagugu gggucaaaaa   9420
aaaaaaaaaa aaa                                                      9433

<210> SEQ ID NO 31
<211> LENGTH: 7480
<212> TYPE: RNA
<213> ORGANISM: Homo sapiens

<400> SEQUENCE: 31

agcguccuug uuuguguggu gccgccgccg ccggugcagc cgucgccgcc gccgcugccc     60
ccgucuguac cgcagugucu gcuccgcccg cccgccccgg uccggcccgc cccccucccc    120
uacccccguc ccuagucccg ucagcagggu cuggaucccc ugugccgucg ccucuuccuu    180
uuucgacgcc uccgccgccg ccugaggagg cgagcuagcc gggaguuaca ccgccaccgc    240
caggauggau agaaugacag aagaugcucu ucgcuugaau cuguugaagc ggagcuugga    300
cccagcagau gagcgagaug auguccuggc aaagcgacuc aaaauggagg ggcaugaggc    360
cauggaacgu cugaaaaugu uggcauugcu caaaaggaag gauuuggcaa aucuugaggu    420
gccacaugag uuacccacca aacaggaugg caguggugc aagggcuaug aagaaaaacu    480
uaacgggaau cucaggccuc auggagacaa caggacugcu ggaaggccag gcaaagaaaa    540
caucaaugau gagccugugg auaugagugc uagacggagu gagccagagc gaggaaggcu    600
aacucccuca ccagacauca uuguuuuguc ugacaaugag gcuuccaguc cccguuccag    660
uuccagaaug gaagaaagac ucaaagcagc caacuuagag auguuuaagg ggaaaggcau    720
ugaggagcgg cagcagcuua ucaagcagcu gagggaugag cuacgauugg aagaagcccg    780
acugguccug uuaaagaaac ugagacagag ucagcuacag aaagagaaug ugguccagaa    840
gacuccaguu guacagaaug cagcaucuau uguucagcca ucuccugccc augugggaca    900
gcagggccua ucuaagcuuc ccucucggcc uggggcccaa gggguugaac cucaaaauuu    960
gagaacauua cagggucaca gugucauccg uucagcuacc aauaccaccc uuccacacau   1020
guugaugucu caacguguua uugcaccaaa cccagcccag cuacaggguc agcggggccc   1080
gccuaagccu ggccuuguac gcaccacaac acccaacaug aaucccgcca ucaauuauca   1140
```

-continued

```
accgcaguca aguucuucug uuccauguca gcguacaaca uccucugcca ucuauaugaa   1200
ccuugcuucu cauauccagc cagggacggu gaacagagug uccucgccac uuccuagccc   1260
cagcgccaug acugaugcug ccaacucaca ggcugcagcc aaauuggcuc uucgcaaaca   1320
gcuggaaaag acacuccugg agaucccacc cccuaaaccu ccugcucccu uacuucauuu   1380
cuugccuagu gcagccaaua gcgaguucau cuacauggua ggcuuggaag aagucguaca   1440
gagugucauu gacagccaag gcaaaagcug ugccucacuu cugcggguug aacccuuugu   1500
augugcccag ugccgcacag auuucacccc ucacuggaag caagaaaaga augguaagau   1560
ucuaugugag caguguauga ccuccaacca gaaaaaggcu cuaaaagcug aacacaccaa   1620
ccggcugaaa aaugcauuug ugaaagcccu acagcaggaa caggaaauug aacagcgauu   1680
acagcagcag gcagcccucu cccccacuac ggcuccagcu guguccagug ucaguaaaca   1740
agagaccauc augagacauc auacgcuucg gcaggcucca cagccccaga gcagccucca   1800
gcguggcaua cccacaucug cccgcuccau gcuuucaaac uuugcacagg caccccaguu   1860
gucugugcca gguggccucc uugguaugcc aggugucaac auugcauacu ugaauacugg   1920
caucggagga cacaaaggcc ccaguuuggc agaccgacag cgugaauacc uuuuagacau   1980
gaucccuccc cggucuauau cgcaguccau caguggacag aaauaacgcc uguuccacuu   2040
guacugcccc auccuugaau ccuuuauccc uuuccucuuu cauucccccca acuucugucg   2100
caugcagugc cuguacuggu gccuaccaua cacggaaagc aaaacagaaa aacagaagac   2160
aaaaaauaga gaucagcaag aaaacacacg cccugcccug ccaccucccc uuuauuucac   2220
acugcugcga ucuguucuuc ugccgcucug ucuucucucu ucaguuuucu uuaacaguga   2280
gguggaucuu uaccucugau agaggucaga augagguccu ggggagaauc uaagcccucc   2340
gaugugugu ucuaaaguug uuuuaugcua uaauuauuac cauuuuuaau gauguugugu   2400
guccucccuu uguucagugg acgguuaaac cuucccccac ucaaccaauc uuuuucuuuu   2460
uccuuuucuu ccuuuuuuuu uuuuuuuuuu guaaacacaa augacauuca guucaaugau   2520
acgagcauug cagauugcag uaggggucccc agcugccaag uaggacauga cuaggagugu   2580
uaggggcaga aguuuugaau gcacuuaacc ggaggagggc gcagggugggg ggguaucaaa   2640
gaaggacgaa uagcacccua ccugugggug uuugggggcu ggacaauuug gguggcagug   2700
uuugguacug aaguugggcu cuaagaauga ggggaaagag ccuggggagg agcuuaaaac   2760
ucaaccacuc uggaauuuac ccauagaaga cgggaagaaa gagguaugaa gaugggcuca   2820
auuaugagcc agggaggauu gaaacuaggu ccugccuuuc uguaucuugg ggaaauaaga   2880
ccgaucuccu gaccccauug ggaacacgga agucuauucc aggccaacca gcccaaaauu   2940
auuucaucuu guauucuuug uaaaauucuc ccucacccca cccugcuuuu aaaaauucua   3000
aucuaucccc ucuaaccaua gccccaucua uaauacagag gaacggcugu uccaaggcug   3060
uuugcugggu gucccacaag uuggguggac auaaaugagu caagugacaa caggaggaaa   3120
uagacuuaga cgaaagaaag gauuucucuu ccaacaguug agauucgcau auuugccuau   3180
ucuuucaccc ucugagugcc aggagaugag aggcuggggg uacacaauca gguuggaguc   3240
cuguccuuac ucugcugcac cagcugcaga accaacugcu caaagccaaa cagcucaugg   3300
caaaaccagc uuaggaccuc ugcuguacaa auaguugcuu cccacugccc cccgcccgcc   3360
cccagaauga uauuaauuuu gccuuuuuuu uuuuuuuuuu uuuaagcgcu acuaauguag   3420
agaaugaauu gaauugugca auguugcugu ucuggggacu ggggagauua gcaucccauu   3480
ugcccacacu gugggaagac ggaguggacc aggcuguuuu ugaaguaagg gaagccccuu   3540
```

-continued

```
aaagguacgg guuucugcuc uucucauagu guacacccac cugccucucu ggcuccagaa   3600
gcugccagag ugcacugggg ggaauguucu cagcagagaa gaaugaggag aaguuuaaua   3660
uuuugcccuu gaaagucacc ugaggaaguu uccccacuuu uauuuuuuaa aauuaaguaa   3720
uuuuuuaaag aaggcacuuu uaaaauuaac acacacauga acugcacacc uuccccauaa   3780
aauuuggagg uggggugggga gaaagagcua aaaucaggcu caguuccccu acucuggccu   3840
cuacucccca caccccagug ccacuguggg ugacuauacu ggcccuacgg gccuuccugg   3900
cuuuuuucuu uccucccuua ccccaaauuc auugagcacu uaaaggagca gagaugcagc   3960
cagugucugg gcuccccccag uggugaaaug aucuggaagc uagaugcuag uaacagguag   4020
ugauuggguu uuuugaguau uuuuccgggg aaugugguac cccugacugu aagugguggg   4080
agagggaggg ggguuaaugg aacugggucu gggauuauuu uaaaauuaua uauauauaua   4140
uaaagauaua uucuuacauc uuuucuuugc ccucugugcu uugaaagcac uggauaaauu   4200
guuugguuuu gcuuuucucu cuuccacaaa auuggaagcu uuuuuuaaaa auguuuuccc   4260
cacaagucau cuugccuugu ggcaugucug ucuagccucu ucccucccucc cucaugauga   4320
agugccauuu cuguuacguc ucccucuccc caagcucaga ggugcucaga gguacgagau   4380
gcccaaguuu gucaguugag auuaaaagua aggaacagag aaugugcaau accgucuggc   4440
ugggggcugu cccugcccug cccugagcug aguccuuucc cugggagcca ggccaccuua   4500
gaaugggguu uggaaguaag auguauagag uuggggaauc auggagaagg aaagccuaua   4560
gucgagugcc ugcuuaggug cugaggucac aggggagaug guggaaucuu cccuguuuuu   4620
aucccccucag ggucaguuac auagaagcug cuucuugacu aguauagcuc ggugacccuu   4680
uguucaaccg cugagguuug auuucuuacc cuuucuucuc cccauuuuca uacucuuccc   4740
agggauuagu gauggaggug aggucucccu aaucauggua aaguguuaac cuuccaccuc   4800
cucccuuccc uccuccuucc ucauccuucu gucuuccuca auucuccguc ucuuuuuuuu   4860
caucacugau ugccuugugu cccuccaagu cuacuuguua cuauccaucu ccaggcucug   4920
ggccguguag acacuaaacc ucaugcccua aggacaggag gaaagacccu cuguuuggag   4980
cauuauuagu agagugagga ucccaccagu ucugccuggc uuccuccauc cccagaggca   5040
cuaaaagcag uauuuuaagg uuggugucuu acucccugga agccugaaau gggugggaaua   5100
gcgguaaggc uugaguaaaa cuaggggaca gagguucuua uuugucgauu uuauuuuaua   5160
auuugaccac agcaucugaa cucccucucu cccuggaaua aguauuuuuc ccacauuuuu   5220
ggauauaugu augguagaca auuuuuuuuu aagacacaga gauaaauguu uuccugcuuu   5280
gguuaccuuu ccuuuccccu uuaaaaggaa uuagcuauag aacugcuuug uaaagaugcu   5340
ucuugauauu uuacuuuugu uccuuuuccc uaaucauucc cuuuucuccc cacuccucca   5400
gaaggcauaa cccuucucuc cacaccccccu acccccaccc ccguccuagg cucccauccu   5460
uuccaucaag accuucauua gcuuaugaua uuugcugccg agauguuaua acaaggacuc   5520
guucauguau auaagcuauu ucuugaucca uuuaaaagga auuguacauu guguagaaaa   5580
aaaaaaaaac cugaaaaaga gaaaaaaaag cccuagccau ggauauugug aaacuguguu   5640
augucauuuu guaaugugcc cguuugugua ugauccgugc aaaaggguuu cuggggaagg   5700
ggaggggggua gggaggcagg gcuguggagg guggguaggg gagugggccg ggcccagcac   5760
acugagacug gcagcugcuc caaccccauc ccuccuuaga gaugccaccu cccccaccac   5820
ccaccccuaa uuugugccuu gccuccccac ccuggaguag ucccuccggg ucaccagcac   5880
ugccuuggca gagcccacuc ccuacccuaa ccugcccacc cucccuaucc cccagcauua   5940
```

-continued

```
gguugauacu gugggaagu gcugggggcu gggagguagc cgaggaaugg ggcaguuccc   6000

gggggcaucg aaaccaagua uuauuaugaa uuguaauugu auuugcacug uuuuuuuccu   6060

cugauugcau cagcauauau acaauauacc uauauaacaa aauucagugu caagcuuucu   6120

uaugcaaggg auuuccccca ccccaccucc ucaaaaaaga aagaaccuag ucuuaugggc   6180

cuuugagggu ggauugucag gggaugauag aaaggauuuu aauaagucau ccugaggaaa   6240

uuucaccuag ugagagccac auccaucugc acagccuuag gcugcgugaa ccgaggugag   6300

gcugagcucc ugugaaagcc aagaccuccu gguccaggac uuuguagagu aaaaagaacc   6360

accaacacaa aaggggguuga gggggcuaca aucuggagac cuggggucuc cuacuaacuu   6420

gcuauaugau cuuugguaga guuaauuuuc ugaguaucaa uuuucuuauc ugugaaguga   6480

agagggggau caucuggcca ccaaguuuaa aauucuauac uucucaccug ccaaaaccaa   6540

aaaacaacuu gaggugagga aaguguuggg cccagaaacc agggaggaac ugaaagugac   6600

ucgcguugaa gugguuaugu guaugacaau gcucuuggag aacugccagu ccucuauggu   6660

uacccuugau uugggagagg cagcagaguc auguccaggg caucagacca gugacaucuu   6720

ugccuuuaug ccucuaguca ucugagggcg gggacuaggc cucaagcccc aucucacagc   6780

caaccacaga gcccuuaagg gugguugaca auugaaugcc ccagguuggu gcuuuaguua   6840

uuuacucccu uugugagcua caggaugugu aacuuuuccc ccaucuuggu gauaaaauag   6900

gagagcgcag acacagccca cauuuugucu ccuuuccuca gauuucaucu gaaccccgcu   6960

aaaggcagcu guuucacagu cugucuccuu caggggccca auuuccccac agccugggcu   7020

gaguacuccu acucucuucu uuagguucug ggcugauaaa gccuggagag gguacagggu   7080

gaugggugaa gcccugguga aggugaaagg auagauuggg guuggggggu ggggagcagg   7140

gaggugggau ggggaauggc cuucccugaa uaggguggu gggaggggaa caagacccuu   7200

uugcacaacu cucuuuaagu uuccuuuauu ucuuuuuuaa cucauucuga uuuucugcau   7260

uguguuuggg aaauaaaaug aaaaaacuaa gaccaauaga aacugguuuu caaaaaggca   7320

aauacacucc caucuguuuc agaugcugcu gagcauuuca gcagugacag auucaaauaa   7380

uaagcuaauu uuuggagaaa ggauuaaaag aaaaaaaaac uuuguaauau uuaucacuug   7440

caagcuaugu uuaauaaaga aaggaauggu uucuaaaaaa                          7480


<210> SEQ ID NO 32
<211> LENGTH: 87
<212> TYPE: RNA
<213> ORGANISM: Artificial Sequence
<220> FEATURE:
<223> OTHER INFORMATION: small RNA

<400> SEQUENCE: 32

ucucaagcug ugagucuaca aagggaagcc cuuucuguug ucuaaaagaa aagaaagugc     60

uucucuuugg ugguuacgg uuugaga                                           87
```

BIOMOLECULAR GROUP RELATED TO CELL ANTI-AGING

TECHNICAL FIELD

The present invention relates to a process for producing a Muse cell-like cell or a method for extending the replicative life span of a cell population.

BACKGROUND ART

The Nobel Prize in Physiology or Medicine 2012 was awarded to Prof. Shinya Yamanaka, who first created iPS cells, and Dr. John Gurdon, who studied the foundation of the above technology. It is expected that the iPS cells will bring a totally novel treatment strategy into pharmaceutical industries.

With regard to the iPS cell-related technology, Patent Literature 1, for example, discloses that introduction of four genes (Oct3/4, Klf4, Sox2, c-Myc) into a cell causes a pluripotent stem cell to be induced from the cell. In addition, with regard to a pluripotent stem cell-related technology, Patent Literature 2, for example, discloses that introduction of three genes (Oct3/4, Klf4, Sox2) and one miRNA (e.g., hsa-miR-372) into a cell causes a pluripotent stem cell to be generated. Further, Non-Patent Literature 1 describes that if the p53 gene is disrupted in a cell to be induced into a pluripotent stem cell when the above four or three genes are introduced, the pluripotent stem cell generation efficiency is increased. Furthermore, Patent Literatures 3 and 4 disclose that a pluripotent stem cell can be generated by introducing, into a cell, a specific RNA strand (e.g., miR-520d-5p).

Meanwhile, there is room for improvement in respect to the regulations of carcinogenesis and differentiation so as to apply iPS cells to clinical practice. Among the efforts, Patent Literature 5 shows the isolation of a cell fraction containing a Muse cell as a novel approach to pluripotent stem cells. This Patent Literature 5 discloses that the Muse cell shown in Patent Literature 5 can differentiate into any type of tissue, is useful as an iPS cell source (having a high efficiency of generating iPS cells), and can be isolated without introduction of any gene.

CITATION LIST

Patent Literature

[Patent Literature 1] WO2007/069666
[Patent Literature 2] WO2009/075119
[Patent Literature 3] WO2012/008301
[Patent Literature 4] WO2012/008302
[Patent Literature 5] Japanese Patent No. 5185443

Non-Patent Literature

[Non-Patent Literature 1] "Suppression of induced pluripotent stem cell generation by the p53-p21 pathway.", Hong et al., Nature, 2009, Aug. 27; 460(7259):1132-5, Epub. Aug. 9, 2009.

SUMMARY OF INVENTION

Technical Problem

Unfortunately, while there are some cases in which pluripotent stem cells have been prepared as described above, approval of the manufacture and marketing of a pharmaceutical-use product has not been granted by the agencies. This is because the research has made only some progress due to limited use of the technology for preparing pluripotent stem cells. Note that when methods with verified side effects (e.g., c-Myc-mediated carcinogenesis during the initial stage of culture) are excluded from the above few methods, effective methods are further limited.

As described above, the novel approach using a Muse cell has been reported. However, the Muse cell disclosed in Patent Literature 5 has to be isolated from an in vivo mesenchymal tissue or cultured mesenchymal cells by using, as an index, the feature where the cell is positive for SSEA-3. Thus, the preparation of the source materials and the isolation of the Muse cell are complicated and costly.

The present invention has been completed in light of the above situations. The purpose of the present invention is to provide, for example, a process for producing a Muse cell-like cell or a method for extending the replicative life span of a cell population.

Solution to Problem

The present inventors found that when expression of ELAVL2, TEAD1, or GATAD2B was inhibited as described in the Examples below, a Muse cell-like cell appeared. Then, the present inventors have completed the present invention. Surprisingly, the replicative life span of the cell preparation was also extended at this time.

Specifically, an aspect of the present invention provides a process for producing a Muse cell-like cell, comprising the step of inhibiting expression or function of ELAVL2, TEAD1, or GATAD2B.

In addition, another aspect of the present invention provides a Muse cell-like cell or a population containing the Muse cell-like cell obtainable by means of the above production process.

In addition, another aspect of the present invention provides a material for regenerative medicine, the material being obtainable by culturing a Muse cell-like cell obtainable by means of the above production process.

In addition, another aspect of the present invention provides a drug or cosmetics comprising the above Muse cell-like cell or population containing the Muse cell-like cell.

In addition, other aspects of the present invention provide a Muse cell-like cell inducer, a drug, cosmetics, or an agent for extending cell population replicative life span, comprising an inhibitor of ELAVL2, TEAD1, or GATAD2B.

In addition, other aspects of the present invention provide: a method for extending cellular or cell population replicative life span, comprising the step of inhibiting expression or function of ELAVL2, TEAD1, or GATAD2B; a process for producing a cell or cell population of which the replicative life span has been extended; a process for producing a cell expressing a high level of CD105 mRNA; a process for producing a fibroblast-producing cell; or a method for activating a Muse cell-like cell.

Advantageous Effects of Invention

According to the present invention, the novel process can be used to produce a Muse cell-like cell. In addition, according to the present invention, the replicative life span of a cell or cell population can be significantly extended.

DESCRIPTION OF EMBODIMENTS

Figure 1:
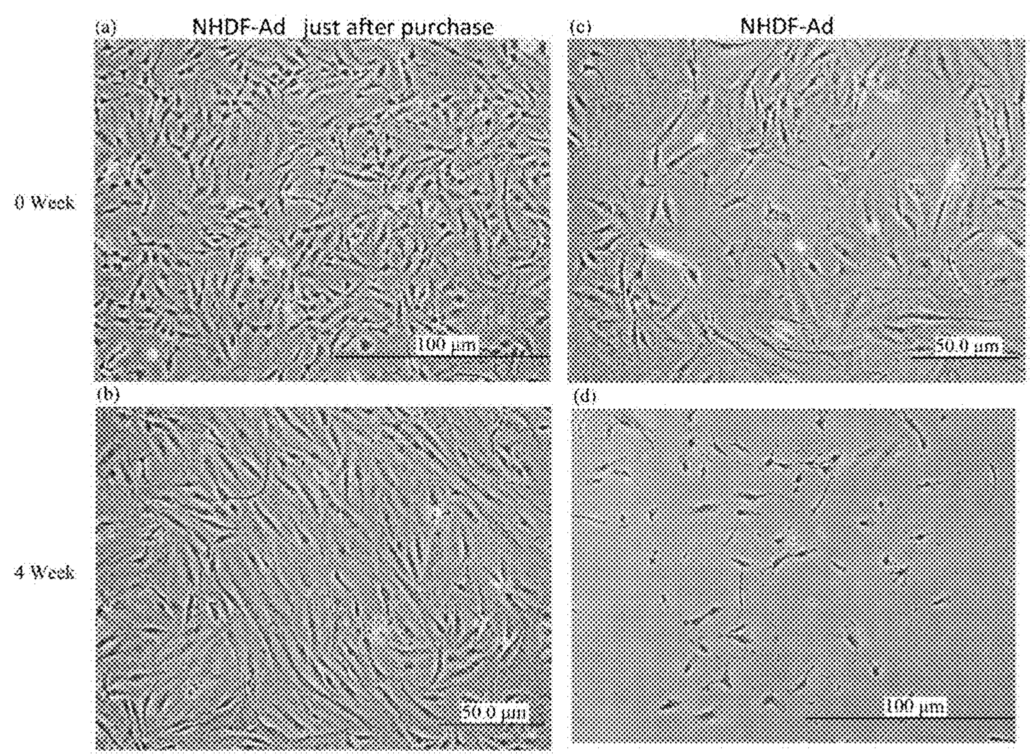
FIG. 1 is photographs of cultured fibroblasts.

Hereinafter, embodiments of the present invention will be described in detail. Note that descriptions are not repeated so as to avoid redundancy.

An embodiment of the present invention provides a novel process for producing a Muse cell-like cell. This production process is a process for producing a Muse cell-like cell, comprising the step of inhibiting the expression or function of ELAVL2, TEAD1, or GATAD2B. This production process can be used to easily produce a Muse cell-like cell or a population containing a Muse cell-like cell. This production process does not necessarily require complicated manipulations, so that the efficiency and cost performance are excellent.

This production process may comprise the steps of: introducing, into a cell population, an RNA strand that inhibits the expression of ELAVL2, TEAD1, or GATAD2B; and collecting a Muse cell-like cell from the cell population into which the RNA strand has been introduced. The above collection may be carried out with reference to, as an index, the cell morphology or gene expression. The above collection includes separation or isolation.

The above Muse cell-like cell may express high levels of endogenous hTERT and SIRT1. The hTERT and SIRT1 are expressed at high levels in juvenile cells. Accordingly, the Muse cell-like cell expressing high levels of hTERT and SIRT1 can be said to be a juvenile cell. In addition, the above Muse cell-like cell may express a high level of endogenous p53. p53 is one of the malignant-tumor suppressor genes, so that the Muse cell-like cell expressing a high level of p53 can be said to have a low risk of developing a malignant tumor.

The above Muse cell-like cell may be positive for CD105, SIRT1, hTERT, P53, Oct4, Nanog, and/or SSEA-3. It is preferable that the levels of expression of CD105, SIRT1, hTERT, P53, Oct4, Nanog, and/or SSEA-3 (hereinafter, sometimes referred to as "CD105, etc.") are significantly higher than those of control samples (e.g., hiPSC (HPS0002 253G1), CD105-knockout cells, normal cells, non-pluripotent cells, or samples derived therefrom). In addition, the levels of expression of CD105, etc., may be 1.1, 1.2, 1.4, 1.6, 1.8, 2.0, 3.0, 4.0, 5.0, 10, 20, 30, 40, 50, 100, 500, or 1000 times higher than those of the control samples. A real-time PCR is a preferable method for measuring the levels of expression of CD105, etc., in view of measurement accuracy and convenience.

The presence of the Muse cell-like cell may be determined using, as an index, whether or not the cell has morphology like an eyeball (with black and white portions). In addition, the Muse cell-like cell may be adherent or floating. Further, the Muse cell-like cell may become an eyeball-like shape, may then be transformed into fibroblast-like morphology, and may finally be returned to the eyeball-like shape. Furthermore, examples of the Muse cell-like cell include the Muse cell described in the above Patent Literature 5 and cells having characteristics substantially equivalent to those of the Muse cell. Whether or not a cell of interest is the Muse cell-like cell may be evaluated by comparing the morphology or the levels of expression of genes therebetween. In this regard, however, it is preferable that the Muse cell-like cell as obtained using the production process according to this embodiment is a more juvenile cell, which has a high level of expression of hTERT, than the Muse cell described in the above Patent Literature 5. Moreover, whether or not a cell of interest is the Muse cell-like cell may be evaluated by determining that the cell of interest expresses a higher level of one of CD105, etc., than the control cells.

The above Muse cell-like cell may have a diameter of 1, 5, 10, 20, 50, 75, or 100 μm. The diameter may be between any two of the above values. From the viewpoint of efficient isolation of the Muse cell-like cell from a cell population, the diameter is preferably 5 μm or greater and more preferably 10 μm or greater.

The details of the nucleotide sequences and other characteristics of ELAVL2, etc., can be obtained from the Web sites of the HGNC (HUGO Gene Nomenclature Committee) or NCBI (National Center for Biotechnology Information). With regard to HGNC IDs according to HGNC, ELAVL2, TEAD1, and GATAD2B have been assigned to HGNC: 3313, HGNC:11714, and HGNC:30778, respectively. The ELAVL2 mRNA may contain the nucleotide sequence set forth in SEQ ID NO: 29. The TEAD1 mRNA may contain the nucleotide sequence set forth in SEQ ID NO: 30. The GATAD2B mRNA may contain the nucleotide sequence set forth in SEQ ID NO: 31. Note that the respective genes have alternative names. These alternative names are designated in the Web sites of the HGNC. Accordingly, the respective genes may be referred to as the alternative names. For example, ELAVL2 include genes called HEL-N1 or HuB.

An embodiment of the present invention provides a process for producing a material for regenerative medicine, comprising the step of culturing the above Muse cell-like cell. Examples of the material for regenerative medicine include organs for regenerative medicine. In addition, another embodiment provides a material for regenerative medicine, the material being obtainable by culturing the above Muse cell-like cell. In addition, another embodiment provides a method for treating a damaged tissue, comprising the step of injecting the above Muse cell-like cell or Muse cell-like cell population into a damaged site. In addition, another embodiment provides a drug for treating a damaged tissue, comprising the above Muse cell-like cell or Muse cell-like cell population. In addition, another embodiment provides an anti-aging method comprising the step of injecting the above Muse cell-like cell or Muse cell-like cell population into a tissue. In addition, another embodiment provides cosmetics for an anti-aging comprising the above Muse cell-like cell or Muse cell-like cell population.

An embodiment of the present invention provides a Muse cell-like cell inducer comprising an inhibitor of ELAVL2, TEAD1, or GATAD2B. When this inducer is used, a Muse cell can be induced from a cell. In addition, when this Muse cell-like cell inducer is given to malignant tumor cells, the malignant tumor can be treated. In addition, the inducer can be used as additives, etc. that help livestock animals grow while the effect of suppressing a malignant tumor, etc., is exerted.

An embodiment of the present invention provides a method for treating a damaged tissue, comprising the step of inhibiting the expression or function of ELAVL2, TEAD1, or GATAD2B in a cell of the damaged tissue. At this time, the cell in the damaged tissue is transformed into a Muse cell and further differentiated, so that the damaged tissue is repaired. In addition, another embodiment provides a drug comprising an inhibitor of ELAVL2, TEAD1, or GATAD2B.

An embodiment of the present invention provides a tissue anti-aging method comprising the step of inhibiting the expression or function of ELAVL2, TEAD1, or GATAD2B in a cell of a tissue. At this time, the cell in the tissue is transformed into a Muse cell and further differentiated, so that the tissue is reconstructed. In addition, another embodiment provides an anti-aging agent or anti-aging cosmetics comprising an inhibitor of ELAVL2, TEAD1, or GATAD2B.

An embodiment of the present invention provides a method for extending cellular or cell population replicative life span, comprising the step of inhibiting the expression or function of ELAVL2, TEAD1, or GATAD2B. According to this method, the cellular or cell population replicative life span can be extended, so that the cells can be cultured for a long period for the purpose of research. In addition, this method is applicable to anti-aging. In addition, another embodiment provides an agent for extending cellular or cell population replicative life span, comprising an inhibitor of ELAVL2, TEAD1, or GATAD2B. The extended period may be 1, 2, 3, 4, 5, 10, 15, 20, 25, 30 weeks or longer. The period may be between any two of the above values. The extended cellular replicative life span may be 6, 7, 8, 9, 10, 15, 18, 20, 25, 30, 40 weeks or longer. The extended cellular replicative life span may be between any two of the above values.

Normal cells replicate to form a tissue. Meanwhile, it has been known that the number of replicative cycles is limited and normal cells cease to divide at a certain time point. This phenomenon that the cells enter a state of growth arrest is generally referred to as cellular senescence. The cellular senescence seems to be responsible for a decrease in tissue functions and/or human aging. This cellular senescence can be actually observed in experiments in vitro. When normal cells are subjected to repeated culture passage, the cells stop proliferation at a certain time point. This provides a barrier to usage of research-use cells, which is a cause of preventing research progress in the field of cell engineering. In addition, use of the method according to the above embodiments enables the cellular or cell population replicative life span to be extended.

An embodiment of the present invention provides a process for producing a cell or cell population of which the replicative life span has been extended, comprising the step of inhibiting the expression or function of ELAVL2, TEAD1, or GATAD2B. According to this production process, a cell or cell population of which the replicative life span has been extended can be easily produced. Because the resulting cell or cell population has extended replicative life span, they are useful for research or regenerative medicine applications etc.

An embodiment of the present invention provides a process for producing a cell expressing a high level of CD105 mRNA, comprising the step of inhibiting the expression or function of ELAVL2, TEAD1, or GATAD2B. According to this production process, the cell expressing a high level of CD105 mRNA can be easily produced. In addition, the resulting cell with a high level of expression of CD105 mRNA can be used for substantially the same applications for the above-described Muse cell-like cell.

An embodiment of the present invention provides a process for producing a fibroblast-producing cell, comprising the step of inhibiting the expression or function of ELAVL2, TEAD1, or GATAD2B. According to this production process, the fibroblast-producing cell can be easily produced. In addition, the resulting fibroblast-producing cell can be used for substantially the same applications for the above-described Muse cell-like cell.

An embodiment of the present invention provides a method for activating a Muse cell-like cell, comprising the step of inhibiting the expression or function of ELAVL2, TEAD1, or GATAD2B. According to this method, the Muse cell-like cell can be easily activated. As used herein, the term "activation" includes an increase in the size of the cell. The size of the cell at this time may be increased 2-, 5-, or 10-fold. The activated Muse cell-like cell can be used for substantially the same applications for the above-described Muse cell-like cell. In addition, another embodiment provides a Muse cell-like cell activator comprising an inhibitor of ELAVL2, TEAD1, or GATAD2B.

An embodiment of the present invention provides a method for treating a malignant tumor, comprising the step of inhibiting the expression or function of ELAVL2, TEAD1, or GATAD2B. In addition, another embodiment provides an anti-malignant tumor drug comprising an inhibitor of ELAVL2, TEAD1, or GATAD2B. Conventional drugs containing a low-molecular-weight compound induce apoptosis to treat a malignant tumor. The treatment method, drug, or inducer according to the embodiments can cause a malignant tumor cell to be induced into a Muse cell-like cell, thereby exhibiting therapeutic efficacy.

Each method or process according to the above embodiments may further comprise the steps of: (a) introducing to a cell an inhibitor of ELAVL2, TEAD1, or GATAD2B; or (b) culturing or growing the cell into which the above inhibitor has been introduced.

An embodiment of the present invention provides a method for increasing a ratio of a Muse cell-like cell to a cell population, comprising the step of causing an inhibitor of ELAVL2, TEAD1, or GATAD2B to contact the cell population. In addition, another embodiment provides a process for producing a cell population in which a ratio of a Muse cell-like cell is increased, comprising the step of causing an inhibitor of ELAVL2, TEAD1, or GATAD2B to contact the cell population.

An embodiment of the present invention provides a research-use or medical kit comprising the above inhibitor. Examples of this kit may include kits for Muse cell-like cell preparation, synthetic organ preparation, anti-aging, or treatment, and kits for extending cellular or cell population replicative life span. This kit may further contain, for example, a buffer, a package insert describing information on an active ingredient, a container for storing an active ingredient, and/or a package.

An embodiment of the present invention provides a method for screening for a Muse cell-like cell inducer, an agent for extending cellular or cell population replicative life span, a Muse cell-like cell activator, an anti-aging agent, anti-aging cosmetics, or a drug, the method comprising the step of selecting a test substance that decreases the expression or function of ELAVL2, TEAD1, or GATAD2B. This method may be used to obtain a Muse cell-like cell inducer, etc. This method may comprise the steps of introducing a test substance into a cell and measuring a level of expression or function of ELAVL2, TEAD1, or GATAD2B.

The "cell" used in an embodiment of the present invention may be a somatic cell. This somatic cell refers to a cell other than reproductive cells and examples include a skin cell and a fibroblast. The somatic cell is usually not pluripotent or lacks pluripotency. In addition, the above somatic cell may be derived from the skin, heart, lung, stomach, intestine, kidney, uterus, aortic tunica adventitia, or mesenchymal tissue. Also, the above cell may be a malignant tumor cell. Examples of the malignant tumor include tumors caused by a mutation in a normal cell. It has been known that a malignant tumor may be generated from any organ or tissue in the body. Once the malignant tumor cells proliferate, a solid thereof infiltrates into and destroys a surrounding normal tissue. Examples of the malignant tumor include carcinoma, sarcoma, hematological malignancies, lung cancer, esophagus cancer, gastric cancer, liver cancer, pancreatic cancer, renal cancer, adrenal cancer, biliary tract cancer, breast cancer, colon cancer, small intestinal cancer, cervical cancer, endometrial cancer, ovarian cancer, bladder cancer, prostate cancer, ureteral cancer, renal pelvis cancer, ureteral cancer, penile cancer, testicular cancer, brain tumor, central nervous system cancer, peripheral nervous system cancer, head and neck carcinoma (e.g., oral cancer, pharyngeal cancer, laryngeal cancer, nasal cancer, paranasal cancer, salivary gland cancer, thyroid cancer), glioma, glioblastoma multiforme, skin cancer, melanoma, thyroid cancer, salivary gland cancer, and malignant lymphoma.

As used herein, the term "endogenous" means that a substance of interest is present depending on an intracellular mechanism. For example, a protein that is constitutively expressed in a cell is included in an endogenous protein as long as the protein is so expressed.

As used herein, the wording "inhibiting the expression of a gene" means the inhibition of transcription of a gene to mRNA or the inhibition of translation of mRNA to a protein or polypeptide. In addition, the examples include the inhibition induced by decomposition of a gene, mRNA, or protein. In the field of biochemistry, examples of a role involving a gene include generating mRNA from the gene, producing a protein encoded by the gene, and causing the protein to exert its activity. Because of this, the wording "inhibiting the function of a gene" as used herein includes a decrease in the production level of mRNA or protein after the expression of the gene is inhibited. Also, the wording "inhibiting the function of a gene" includes a decrease in the activity of the mRNA or protein encoded by the gene.

As used herein, the wording "a state in which the expression is inhibited" includes a state in which the level of expression is significantly decreased when compared with that in a normal state. The above "significantly decreased" may refer to a state in which the level of expression is decreased to 0.35 or less, 0.3, 0.2, 0.1, 0.05, 0.01, or 0 times the level of expression. The level may be decreased to between any two of the above values. A Muse cell-like cell may be stably induced. Also, the cellular or cell population replicative life span may be reliably extended. From these viewpoints, the level is decreased to preferably 0.2 or less times the level and more preferably 0.1 or less times the level. Note that the level of expression may be determined by using, as an index, the level of mRNA or protein. In addition, as used herein, the term "significantly" may include a case of $p<0.05$ when Student's t test (one-sided or two-sided) is used to evaluate a statistically significant difference. Also, the term may include a state in which there is a substantial difference. Note that the intensity of inhibition with respect to a "state in which the function is inhibited" may also refer to the intensity of inhibition with respect to the inhibition of expression in substantially the same manner as in some embodiments.

As used herein, examples of the "form of an inhibitor" include, but are not particularly limited to, an RNA strand, DNA strand, low-molecular-weight organic compound, antibody, and polypeptide. Examples of the above RNA strand that can be used include RNA strands (e.g., siRNA, shRNA, or small RNA) having RNAi activity against ELAVL2, TEAD1, or GATAD2B. Examples of the above DNA strand that can be used include DNA strands encoding the above RNA strands. The form of the DNA strand may be, for example, a vector. The above low-molecular-weight organic compound may be produced using combinatorial chemistry or HTS (high-throughput screening). For the combinatorial chemistry, an automated synthesizer, an L-COS series (SHOKO, Inc.), for example, may be used. For the HTS, an Octet system (ForteBio, Inc.), for example, may be used. The above antibody may be generated using a known antibody-generating method (e.g., a method disclosed in Clackson et al., Nature, Aug. 15, 1991, 352 (6336), 624-628) or may be purchased from a service company (e.g., EVEC, Inc.). At this time, an antibody library may be constructed and it is preferable to select an antibody with increased inhibitory activity. The above polypeptide can be purchased from a service company (e.g., Wako Pure Chemical Industries, Ltd.). In addition, the inhibitor contains a substance that inhibits the expression or function of a target. Preferably, the inhibitor is less toxic or a substance with substantially no cell toxicity. In this case, when the inhibitor is administrated in vivo, the adverse effects can be suppressed. Here, the cell toxicity or adverse effects may be suppressed and a Muse cell-like cell may then be stably induced. Also, the cell toxicity or adverse effects may be suppressed and the cellular or cell population replicative life span may then be reliably extended. From these viewpoints, it is preferable that the inhibitor is an RNA strand with RNAi activity or a DNA strand with a DNA sequence encoding the RNA strand. Note that when particularly indicated, hsa-miR-520d-5p, nucleic acid containing this guide strand, nucleic acid substantially equivalent thereto, or nucleic acid from which the former is expressed may be excluded from the form of the inhibitor.

As used herein, the term "RNAi" includes phenomena in which siRNA, shRNA, miRNA, short or long single or multi-stranded RNA, and/or modification products thereof are used to suppress or silence the function of a target gene or mRNA, etc. Generally speaking, the RNAi-mediated suppression mechanism is specific to its sequence and is present across various organisms. In the case of siRNA or shRNA, the RNAi mechanism in typical mammals is described below. First, a vector that can express siRNA or shRNA is introduced into a cell. After the siRNA or shRNA is expressed in the cell, the siRNA or shRNA becomes a single strand and a RISC (RNA-induced Silencing Complex) is then formed. The RISC uses the incorporated single-strand RNA as a guide molecule to recognize a target RNA strand with a sequence highly complementary to this single-strand RNA. The target RNA strand is cut by an enzyme, such as AGO2, in the RISC. After that, the cut target RNA strand is decomposed. The above illustrates an example of the mechanism. Note that, a plurality of the RNA strands with RNAi activity or the DNA strands encoding each RNA strand may be introduced into a cell. The number of strands introduced may be 1, 2, 3, 4, 5, 6, 8, 10, 20, or more. The number may be between any two of the above values. In addition, from the viewpoint of stably suppressing the function of a target gene or mRNA, etc., the RNA strand with RNAi activity is preferably a single strand or a double strand.

When the RNA strand with RNAi activity is designed, Stealth RNAi designer (Invitrogen) and/or siDirect 2.0 (Naito et al., BMC Bioinformatics, Nov. 30, 2009, 10:392), for example, may be used. In addition, the service provided by a service company (e.g., GeneCopoeia, Inc., Thermo Scientific, Inc.) may be used. The RNAi activity may be verified by quantifying the level of expression of the RNA strand by using a real-time RT-PCR. The RNAi activity may be analyzed with respect to the level of expression of the RNA strand by using Northern blotting and/or may be analyzed with respect to the level of the protein by using Western blotting as well as may be verified using a method such as phenotype observation. The real-time RT-PCR protocol, in particular, is efficient.

As used herein, the term "siRNA" includes an RNA strand which can induce RNAi. Generally speaking, the siRNA double strand may be separated into a guide strand and a passenger strand. Then, the guide strand is incorporated into a RISC. The guide strand incorporated into the RISC is used for recognition of a target RNA. Meanwhile, synthetic RNA is primarily used in RNAi research. However, it has been known that endogenous counterparts exist in vivo. The above guide strand may be composed of RNA containing 15 or more nucleotides. If the number of nucleotides is 15 or more, the RNA is likely to bind specifically to a target polynucleotide. In addition, the above guide strand may be composed of RNA containing 40 or less nucleotides. When the number of nucleotides is 40 or less, there is a lower risk of disadvantageous phenomena such as interferon responses etc.

As used herein, the term "shRNA" includes a single RNA strand that can induce RNAi and can produce a structure (a hairpin-like structure) in which the RNA is bent like a hairpin. The shRNA is typically cut in a cell into siRNA by a Dicer. This siRNA is known to cause a target RNA to be cut. The above shRNA may be composed of 35 or more nucleotides. If the number of nucleotides is 35 or more, a particular hairpin-like structure is likely to be specifically formed in the shRNA. In addition, the above shRNA may be composed of RNA containing 100 or less nucleotides. When the number of nucleotides is 100 or less, there is a lower risk of disadvantageous phenomena such as interferon responses etc. In this connection, many pre-miRNAs, the structure and function of which are similar to those of common shRNA, have about 100 or more nucleotides. Accordingly, the length of shRNA is not necessarily limited to 100 nucleotides or less, which seem to be functional as the length of shRNA.

As used herein, the term "miRNA" includes an RNA strand with a function similar to that of siRNA. The miRNA has been known to be involved in the translational suppression and/or decomposition of a target RNA strand. The difference between miRNA and siRNA resides generally in their biosynthesis pathways and detailed mechanisms.

As used herein, the term "small RNA" refers to a relatively small RNA strand. The examples include, but are not limited to, siRNA, shRNA, miRNA, antisense RNA, and single or multi-stranded low-molecular-weight RNA. Use of the small RNA enables disadvantageous phenomena such as interferon responses to be suppressed.

The above RNA strand may contain a 5' or 3' nucleotide overhang consisting of 1 to 5 nucleotides. In this case, the RNAi efficiency seems to increase. The number of nucleotides may be, for example, 5, 4, 3, 2, or 1. The number may be between any two of the above values. The overhang may be, for example, ac, c, uc, ag, aa, or uu. From the viewpoint of stably exerting RNAi activity, the overhand is preferably ac, c, or uc at the 3' end. In addition, when the above RNA strand is a double strand, mismatched RNA nucleotides may be present between the respective RNA strands. The number of the nucleotides may be, for example, 1, 2, 3, 4, 5, or 10 or less. The number may be between any two of the above values. The above RNA strand may contain a hairpin loop. The number of nucleotides in the hairpin loop may be, for example, 10, 8, 6, 5, 4, or 3. The number may be between any two of the above values. The nucleotide sequence of the hairpin loop may be, for example, gugcuc or cucuuga. This nucleotide sequence may have one or several nucleotide deletions, substitutions, insertions, or additions as long as they can exert desired effects. Note that regarding the arrangement of each nucleotide sequence, the left side is the 5' end and the right side is the 3' end.

In addition, the nucleotide length of the above RNA strand may be, for example, 15, 16, 17, 18, 19, 20, 21, 22, 23, 24, 25, 26, 27, 28, 29, 30, 31, 32, 33, 34, 40, 50, 60, 80, 100, 200, or 500. The length may be between any two of the above values. If the number of nucleotides is 15 or more, the RNA is likely to bind specifically to a target polynucleotide. When the number of nucleotides is 100 or less, there is a lower risk of disadvantageous phenomena such as interferon responses when the RNA strand is administered in vivo. The interferon responses, in general, have been known as a phenomenon in which a cell senses dsRNA and then becomes resistant to viruses.

As used herein, the term "RNA strand" includes a configuration in which a plurality of RNAs or equivalents thereof bind to one another. As used herein, the term "DNA strand" includes a configuration in which a plurality of DNAs or equivalents thereof bind to one another. Examples of this RNA strand and DNA strand include a single or multi-stranded (e.g., a double strand) RNA or DNA strand. The RNA or DNA strand may be conjugated to, for example, a substance that promotes their incorporation into a cell (e.g., PEG or derivatives thereof), a label (e.g., a fluorescent label), a linker (e.g., a nucleotide linker), or a chemotherapeutic agent (e.g., an anti-malignant tumor substance). The RNA or DNA strand can be synthesized using a nucleic acid synthesizer. In addition, the RNA or DNA strand can be purchased from a service company (e.g., Invitrogen, Inc.). The RNA or DNA strand in a living body may form a salt or a solvate. In addition, the RNA or DNA strand in a living body may be chemically modified. The term "RNA strand"

or "DNA strand" includes: an RNA or DNA strand in which a salt or a solvate is formed; a chemically-modified RNA or DNA strand; and others. In addition, the RNA or DNA strand may be an RNA strand analog or a DNA strand analog. Examples of the "salt" include, but are not particularly limited to, anionic salts that are formed using any acidic group (e.g., carboxyl) and cationic salts that are formed using any basic group (e.g., amino). Examples of the salts include inorganic or organic salts. For example, the salts disclosed in Berge et al., J. Pharm. Sci., 1977, 66, 1-19 are included. In addition, the examples further include metal salts, ammonium salts, salts with organic base, salts with inorganic acid, and salts with organic acid. The above term "solvate" refers to a compound formed by a solute and a solvent. J. Honig et al., The Van Nostrand Chemist's Dictionary P650 (1953) can be consulted regarding the solvate. If the solvent is water, the solvate formed is a hydrate. Preferably, the solvent does not interfere with the biological activity of the solute. Examples of the preferable solvent include, but are not limited to, water and various buffers. Examples of the above "chemical modifications" include modifications using PEG or derivatives thereof, fluorescein modifications, and biotin modifications.

In addition, from the viewpoint of stably exerting RNAi activity, the above RNA strand preferably contains a nucleotide sequence complementary to part of the nucleotide sequence of a target gene-derived mRNA. The number of nucleotides included in the above "part" may be, for example, 5, 10, 15, 18, 19, 20, 21, 22, 23, 24, 25, 26, 27, 28, 29, 30, 35, 40, 50, or more. The number may be between any two of the above values.

The plasmids used to generate siRNA or shRNA against a particular gene can be purchased from a service company (e.g., GeneCopoeia. Inc., Thermo Scientific, Inc.). In the below-described Examples, a validated shRNA clone set was purchased from GeneCopoeia, Inc., and was then used. The validated shRNA clone set used in the below-described Example 1 contains four plasmids that can be used to generate ELAVL2 siRNA, four plasmids that can be used to generate TEAD1 siRNA, and four plasmids that can be used to generate GATAD2B siRNA. The nucleotide sequences of the four plasmids that can be used to generate the ELAVL2 siRNA used in the following Example 1 are set forth in SEQ ID NO: 25, 26, 27, or 28. The DNA sequence encoding TEAD1 shRNA or GATAD2B shRNA was inserted into a psiLv-U6TM vector to generate eight plasmids that can be used to generate TEAD1 siRNA or GATAD2B siRNA, respectively, used in the below-described Example 1.

The shRNA containing a nucleotide sequence set forth in SEQ ID NO: 5, 6, 7, or 8 is generated from the four respective plasmids from which ELAVL2 siRNA used in the following Example 1 can be produced. The shRNA can be considered to be cut in a cell by an enzyme to generate siRNA. These siRNAs include the nucleotide sequence set forth in SEQ ID NO: 1 (uuauugguguuaaagucacgg), SEQ ID NO: 2 (aauacgagaaguauaaugcg), SEQ ID NO: 3 (uuuguuugucuuaaaggag), or SEQ ID NO: 4 (auuugcaucucugauagaagc). The nucleotide sequence set forth in SEQ ID NO: 1, 2, 3, or 4 is a nucleotide sequence complementary to part of ELAVL2 mRNA and is considered to be a portion serving as a guide strand.

The shRNA containing a nucleotide sequence set forth in 13, 14, 15, or 16 is generated from the four respective plasmids from which TEAD1 siRNA used in the following Example 1 can be produced. The shRNA can be considered to be cut in a cell by an enzyme to generate siRNA. These siRNAs include the nucleotide sequence set forth in SEQ ID NO: 9 (uuggcuuaucugcagaguc), SEQ ID NO: 10 (gcuuguuaugaauggcag), SEQ ID NO: 11 (guaagaaugguuggcaugc), or SEQ ID NO: 12 (aguuccuuuaagccaccuu). The nucleotide sequence set forth in SEQ ID NO: 9, 10, 11, or 12 is a nucleotide sequence complementary to part of TEAD1 mRNA and is considered to be a portion serving as a guide strand.

The shRNA containing a nucleotide sequence set forth in 21, 22, 23, or 24 is generated from the four respective plasmids from which GATAD2B siRNA used in the following Example 1 can be produced. The shRNA can be considered to be cut in a cell by an enzyme to generate siRNA. These siRNAs include the nucleotide sequence set forth in SEQ ID NO: 17 (caacagauucaagcgaaga), SEQ ID NO: 18 (caauagaugcugcauucug), SEQ ID NO: 19 (caucaacaugugugaagg), or SEQ ID NO: 20 (aggauguuguacgcugaca). The nucleotide sequence set forth in SEQ ID NO: 17, 18, 19, or 20 is a nucleotide sequence complementary to part of GATAD2B mRNA and is considered to be a portion serving as a guide strand.

According to an embodiment of the present invention, ELAVL2 siRNA may contain a nucleotide sequence complementary to the nucleotide sequence set forth in SEQ ID NO: 1, 2, 3 or 4 (e.g., a nucleotide sequence at positions 1 to 21 of the nucleotide sequence set forth in SEQ ID NO: 5, a nucleotide sequence at positions 1 to 21 of the nucleotide sequence set forth in SEQ ID NO: 6, or a nucleotide sequence at positions 1 to 19 of the nucleotide sequence set forth in SEQ ID NO: 7, or a nucleotide sequence at positions 1 to 21 of the nucleotide sequence set forth in SEQ ID NO: 8). According to an embodiment of the present invention, TEAD1 siRNA may contain a nucleotide sequence complementary to the nucleotide sequence set forth in SEQ ID NO: 9, 10, 11 or 12 (e.g., a nucleotide sequence at positions 1 to 19 of the nucleotide sequence set forth in SEQ ID NO: 13, a nucleotide sequence at positions 1 to 18 of the nucleotide sequence set forth in SEQ ID NO: 14, or a nucleotide sequence at positions 1 to 19 of the nucleotide sequence set forth in SEQ ID NO: 15, or a nucleotide sequence at positions 1 to 19 of the nucleotide sequence set forth in SEQ ID NO: 16). According to an embodiment of the present invention, GATAD2B siRNA may contain a nucleotide sequence complementary to the nucleotide sequence set forth in SEQ ID NO: 17, 18, 19 or 20 (e.g., a nucleotide sequence at positions 1 to 19 of the nucleotide sequence set forth in SEQ ID NO: 21, 22, 23, or 24).

According to an embodiment of the present invention, as long as the nucleotide sequences set forth in SEQ ID NOs: 1 to 40 exert desired effects, they may be at least one nucleotide sequence selected from the group consisting of: (c) nucleotide sequences having one or several nucleotide deletions, substitutions, insertions, or additions in any of the above nucleotide sequences; (d) nucleotide sequences having 90% or more homology to any of the above nucleotide sequences; and (e) nucleotide sequences of polynucleotides specifically hybridizing, under a stringent condition, with polynucleotides having nucleotide sequences complementary to any of the above nucleotide sequences. As used herein, the term "complementary nucleotide sequence" refers to a nucleotide sequence of one polynucleotide that is highly complementary to and can hybridize with another polynucleotide. The term "hybridizing" refers to a characteristic in which base pairs can be formed, via a hydrogen bond between bases, between polynucleotides. The base pairs can occur as Watson-Crick base pairs, Hoogsteen base pairs, or any other sequence-specific forms. A state where two single strands are hybridized is called a double strand.

The above term "one or several" may mean that the number is, for example, 10, 8, 6, 5, 4, 3, or 2. The number may be equal to or smaller than any of the above values. Here, the Muse cell-like cell may be stably induced. Also, the cellular or cell population replicative life span may be reliably extended. From these viewpoints, a smaller number is preferable. It has been known to those skilled in the art that RNA strands having one or several nucleotide deletions, additions, insertions, or substitutions can maintain their biological activities.

The above term "90% or more" may mean that the number is, for example, 90, 95, 96, 97, 98, 99, or 100%. The number may be between any two of the above values. Here, the Muse cell-like cell may be stably induced. Also, the cellular or cell population replicative life span may be reliably extended. From these viewpoints, a larger number is preferable. The above term "homology" may refer to a ratio of the number of identical nucleotides between two or among a plurality of nucleotide sequences to the total number of nucleotides as calculated in accordance with a method known in the art. Before the calculation of the ratio, nucleotide sequences selected from the group of nucleotide sequences compared are aligned. If the ratio needs to be optimized with respect to the identical nucleotides, gaps are inserted in some portions of the nucleotide sequences. Alignment methods, ratio calculation methods, comparison methods, and related computer programs have been conventionally well-known in the art (e.g., BLAST, GENETYX). As used herein, unless otherwise indicated, the term "homology" can be represented by a value determined by the NCBI BLAST program. Blastn can be used in default setting as an algorithm when BLAST is used for nucleotide sequence comparison.

The following conditions, for example, can be used as the above "stringent condition". (1) A low ionic strength solution is used for washing at a high temperature (e.g., a 50° C. solution containing 0.015 M sodium chloride, 0.0015 M sodium citrate, 0.1% sodium dodecyl sulfate). (2) A denaturing agent such as formamide is used during hybridization (e.g., a 42° C. solution containing 50% (v/v) formamide, 0.1% bovine serum albumin, 0.1% Ficoll, 0.1% polyvinylpyrrolidone, 50 mM sodium phosphate buffer (pH 6.5), 750 mM sodium chloride, and 75 mM sodium citrate). (3) A filter is incubated overnight at 37° C. in a solution containing 20% formamide, 5×SSC, 50 mM sodium phosphate (pH 7.6), 5×Denhardt's solution, 10% dextran sulfate, and 20 mg/ml denatured, sheared salmon sperm DNA and is then washed at about 37 to 50° C. with 1×SSC. Note that the concentration of formamide may be 50% or more. The washing time may be 5, 15, 30, 60, 120 minutes or longer. A plurality of factors such as a temperature and a salt concentration seem to affect the stringency of a hybridization reaction. The details can be found in Ausubel et al., Current Protocols in Molecular Biology, Wiley Interscience Publishers, (1995).

The above inhibitor can be introduced into cells and the cells can be cultured in accordance with a method known in the art. Examples of the available method for introduction into a cell include infection using a viral vector, a calcium phosphate method, lipofection, electroporation, and microinjection. In addition, drug resistance and a cell sorter, for example, may be used to select only the cell into which the inhibitor has been introduced. Examples of the available medium include media for keeping cells undifferentiated (e.g., pluripotent stem cell medium, ReproStem medium, primate ES cell medium (COSMO BIO Co., Ltd.) and regular human cell media (e.g., DMEM- or RPMI-based medium). For example, the culturing may be performed in ReproStem medium supplemented with 10% FBS under conditions at 37° C. and 5% $CO_2$. These numerical values may have a deviation of, for example, 10, 20, or 30%. The cells may be established or cultured without feeder cells. The number of days of culturing until the Muse cell-like cell is established may be, for example, 1, 2, 3, 4, 5, 6, 8, 10, 15, 30, 60, 100, or more. The number may be between any two of the above values. Here, the Muse cell-like cell may be stably induced. Also, the cellular or cell population replicative life span may be reliably extended. From these viewpoints, the cells into which the inhibitor is introduced are preferably fibroblasts. In addition, when the above RNA strand is introduced into a cell, a plurality of RNA strands may be combined and introduced into the cell. Further, when the above DNA strand is introduced into a cell, a plurality of DNA strands may be introduced into the cell. Here, the numbers of the "RNA strands" and "DNA strands" maybe 2, 3, 4, 5, 10, 20, or more.

As used herein, examples of the available "vector" include viral vectors (e.g., lentivirus, adenovirus, retrovirus, or HIV vectors), *E. coli*-derived plasmids (e.g., pBR322), *Bacillus subtilis*-derived plasmids (e.g., pUB110), yeast-derived plasmids (e.g., pSH19), bacteriophages (e.g., a λ phage), psiCHECK-2, pA1-11, pXT1, pRc/CMV, pRc/RSV, pcDNAI/Neo, pSUPER (OligoEngine, Inc.), BLOCK-it Inducible H1 RNAi Entry Vector (Invitrogen. Inc.), and pRNATin-H1.4/Lenti (GenScript, corp., NJ, USA). The above vectors each contain, for example, a promoter, a replication origin, and/or an antibiotic resistance gene, which are essential components for expression of the DNA strand. The above vectors may be what is called an expression vector.

As used herein, the term "cell population" refers to a population containing a plurality of cells. This cell population may be, for example, a population containing substantially uniform cells. In addition, the cell population may be a cell preparation. The cell preparation may contain, for example, cells and a buffer or medium components. The Muse cell-like cell population may contain, for example, 80, 90, 95, 96, 97, 98, 99, or 100% of a Muse cell-like cell. The content may be between any two of the above values.

As used herein, the term "treatment" includes exerting a prophylactic effect or a symptom-improving effect on a disease (including fibrosis) of a subject or on one or more symptoms involving the disease. As used herein, the "drug" may be a pharmaceutical composition containing at least one pharmacologically acceptable carrier. The pharmaceutical composition can be manufactured by any process known in the technical field of drug formulation. Examples of the process include: mixing an active ingredient with the above carrier. In addition, the dosage form of the drug is not limited as long as the drug can be used for treatment. The drug may be an active ingredient alone or a mixture of an active ingredient and any component. Further, examples of the dosage form of the above carrier include, but are not limited to, a solid and a liquid (e.g., a buffer). Note that examples of a drug for malignant tumor include: an agent (prophylactic) for preventing a malignant tumor; an inducer for ameliorating a malignant tumor; and an inducer for producing a normal stem cell.

A drug administration route effective in treatment is preferably used. Examples of the administration route include intravenous, subcutaneous, intramuscular, intraperitoneal, and oral administration. Examples of the dosage form may include an injection, a capsule, a tablet, and granules. When a polynucleotide is administered, use of an injection is effective. An aqueous solution for an injection may be stored in, for example, a vial or a stainless container. In addition, the aqueous solution for an injection may be formulated with, for example, a saline solution, sugar (e.g., trehalose), NaCl, or NaOH. Further, the drug may be formulated with, for example, a buffer (e.g., a phosphate buffer) and/or a stabilizer.

Examples of the dosage include, but are not particularly limited to, 0.0001 mg to 1000 mg/kg body weight per dosing. An administration interval is not particularly limited, but may be, for example, once every 1 to 10 days. In addition, the dosage, the administration interval, and the administration method can be appropriately selected depending on the age, weight, symptom, affected organ, etc., of a subject. In addition, the administration may be combined with a suitable chemotherapeutic agent. Further, the drug preferably contains a therapeutically effective amount or a dose, which is effective in exerting a desired effect, of active ingredient. One may judge such that when a marker for a malignant tumor is decreased after dosing, there is a therapeutic effect.

As used herein, examples of the “subject” include a human and non-human mammals (e.g., at least one of a mouse, guinea pig, hamster, rat, mouse, rabbit, pig, sheep, goat, cow, horse, cat, dog, marmoset, monkey, and chimpanzee).

Various embodiments when the above ELAVL2, TEAD1, or GATAD2B is inhibited are applicable to the cases where the activity of the RNA strand or protein derived from at least one of them is inhibited (in this respect, however, an embodiment related specifically to a certain gene function is excluded). Such embodiments are included as an embodiment of the present invention. For example, an embodiment of the present invention provides a process for producing a Muse cell-like cell or a method for extending cellular or cell population replicative life span, comprising the step of inhibiting the activity of an RNA strand or protein derived from ELAVL2, TEAD1, or GATAD2B.

As used herein, the term or may be used when at least one matter listed in the text of specification can be employed. The same applies to the term “or”. As used herein, when the wording “between any two of the above values” is indicated, the two values are inclusive in the range.

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention will be further illustrated by referring to Examples. The present invention, however, is not limited to them.

[Experimental Example 1] Culturing of Fibroblasts

Human adult fibroblasts (NHDF-Ad, TakaraBio, Inc.) were purchased. Then, the fibroblasts were cultured in FBM+FGM-2 medium (Ronza, Inc.) at 37° C. for 4 weeks. As a result, cellular senescence was observed (FIG. 1).

FIG. 1A is an image at day 0 of the purchased NHDF-Ad. FIG. 1B is an image of the cells of FIG. 1A after 4 weeks of culturing. FIG. 1C shows the cells that had once been stored after one month of culturing of the above NHDF-Ad and were then reseeded for the purpose of culturing again. FIG. 1D is an image of the cells of FIG. 1C after 4 weeks of culturing.

Example 1

Each plasmid DNA (a validated shRNA clone set) used to generate ELAVL2 siRNA, TEAD1 siRNA, or GATAD2B siRNA was purchased from GeneCopoeia, Inc. Each plasmid DNA was introduced with a Virapower (for increasing transfection efficiency; Invitrogen, Inc.) into a human renal mesangial cell line (293FT cells). Next, lentivirus particles as produced into culture medium (supernatant) were ultracentrifuged and separated as a pellet. Then, the titer was measured using a miR-X lenti titration kit (TakaraBio, Inc.) and human adult fibroblasts (NHDF-Ad, TakaraBio, Inc.) were infected with the resulting lentivirus while the intended MOI was set to 1. After that, the transformed cells were evaluated with respect to a change in the cell morphology, the expression of genes (e.g., Muse cell markers (e.g., CD105, Oct4, Sirt1, hTERT, Nanog), pluripotency markers, aging markers, senescence markers), and the collagen productivity. The above results will be explained in the following (1) to (3).

(1) Change in Cell Morphology

Figure 2:
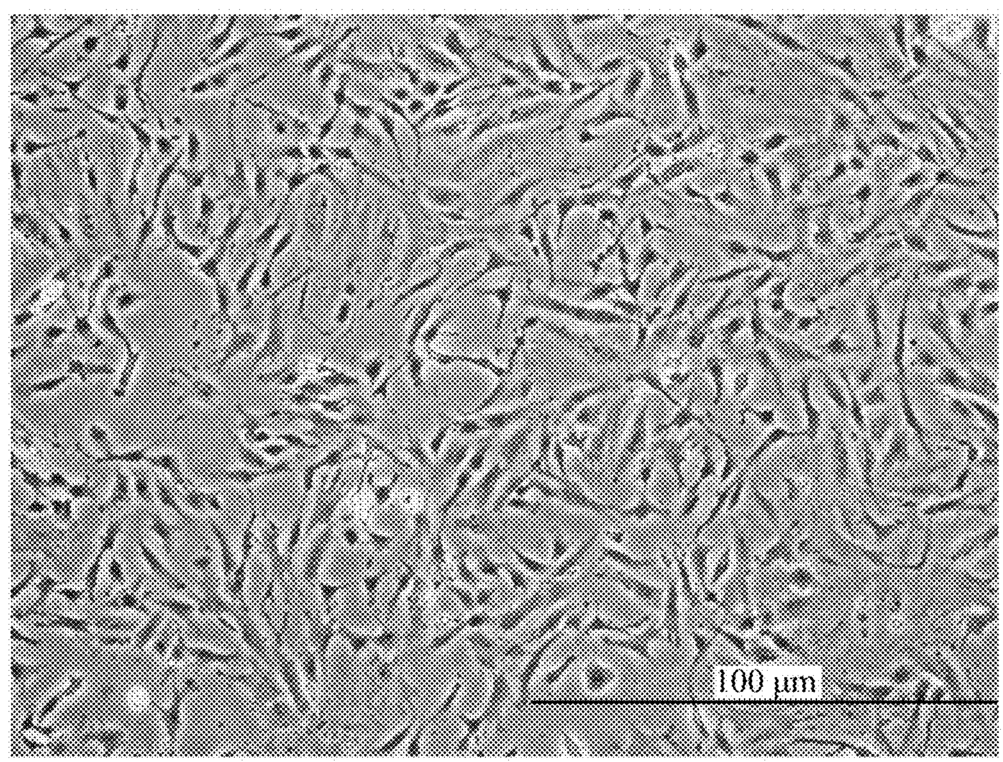
FIG. 2 is a photograph of fibroblasts at Day 0 of culturing.

The cell morphology was observed with an inverted electron microscope. The expression of GFP was observed under a fluorescence microscope (KEYENCE CORPORATION) and was used as a proof of the gene-introduced cell. FIG. 2 is a photograph of the cell at day 0 of culturing.

Figure 3:
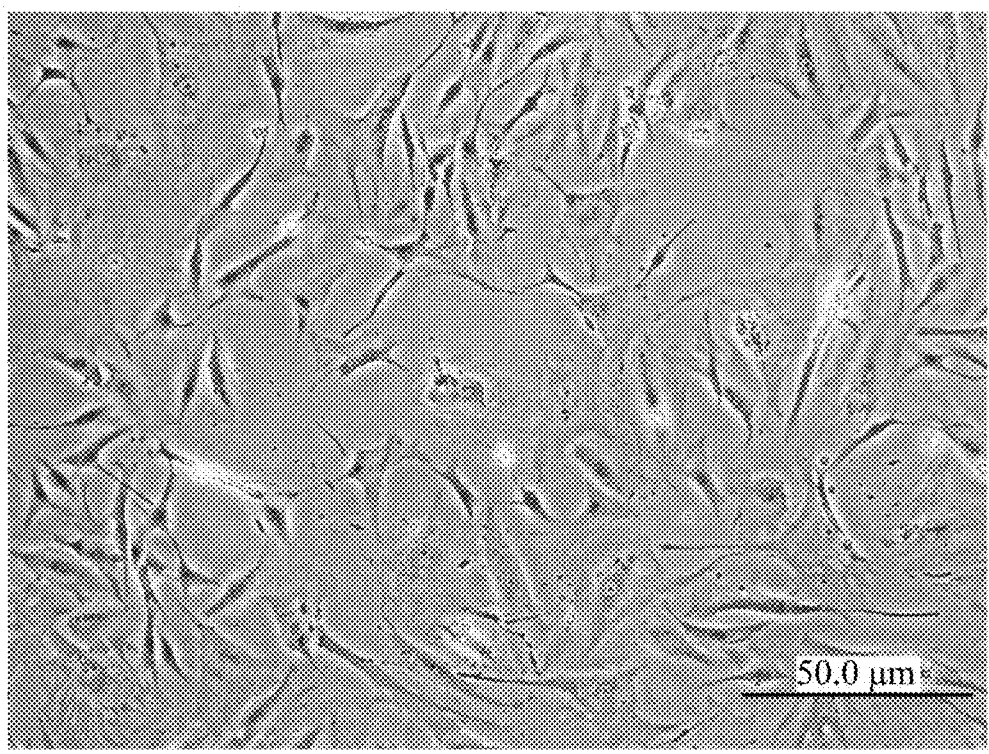
FIG. 3 is a photograph of fibroblasts cultured for 1 month.

FIG. 3 is a photograph of the cell after one month of culturing. The number of cells decreased, indicating that the cellular senescence occurred. Note that the cells were split 4 to 5 times during the one month of culturing.

Figure 4:
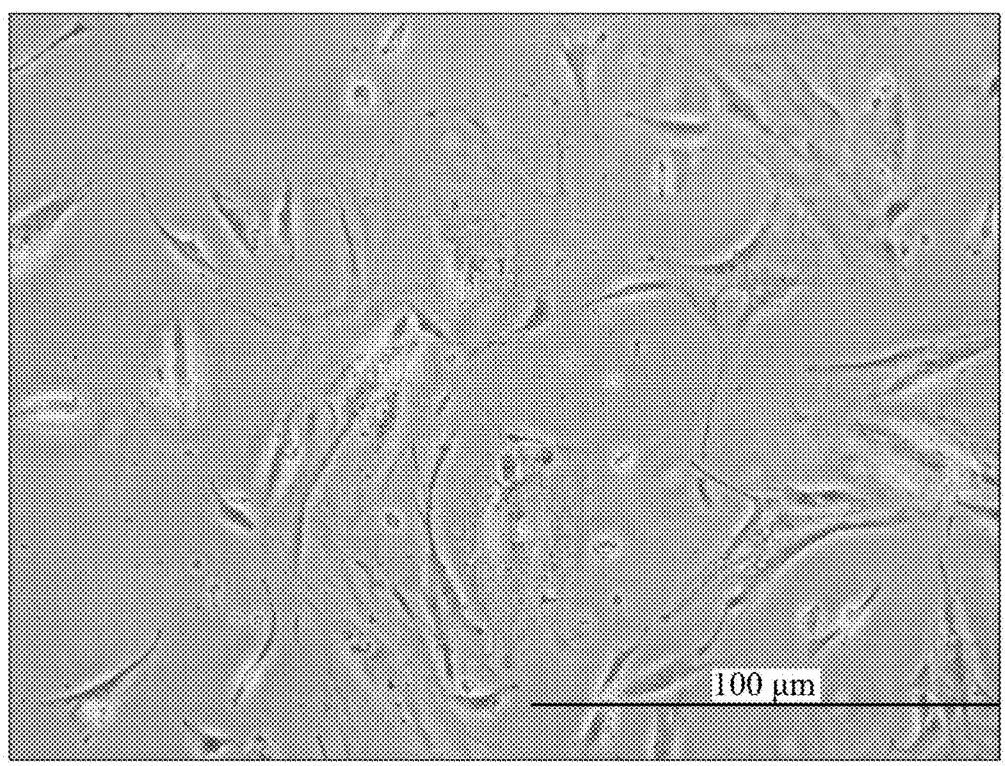
FIG. 4 is a photograph of fibroblasts cultured for one month and three weeks.

FIG. 4 is a photograph of the cell after one month and three weeks of culturing. The number of cells further decreased when compared with that of FIG. 3, indicating that the cellular senescence further proceeded.

Figure 5:
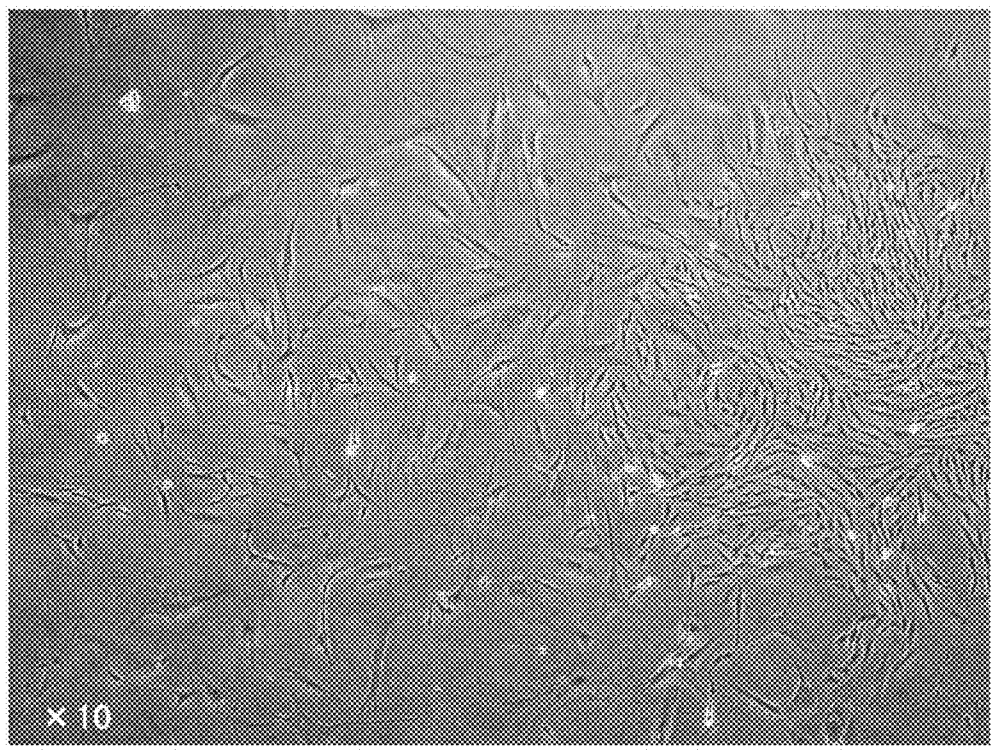
FIG. 5 is a photograph of fibroblasts that were infected with lentivirus after one month of culturing and then cultured for further three weeks.

FIG. 5 is a photograph showing the cells obtained by infecting the cells at one month of culturing (represented by FIG. 3) with the lentivirus, followed by three weeks of culturing. As shown in the right side of the photograph, a dense cell population was observed. This means that the cellular senescence progression was suppressed and juvenile cells were produced.

Figure 6:
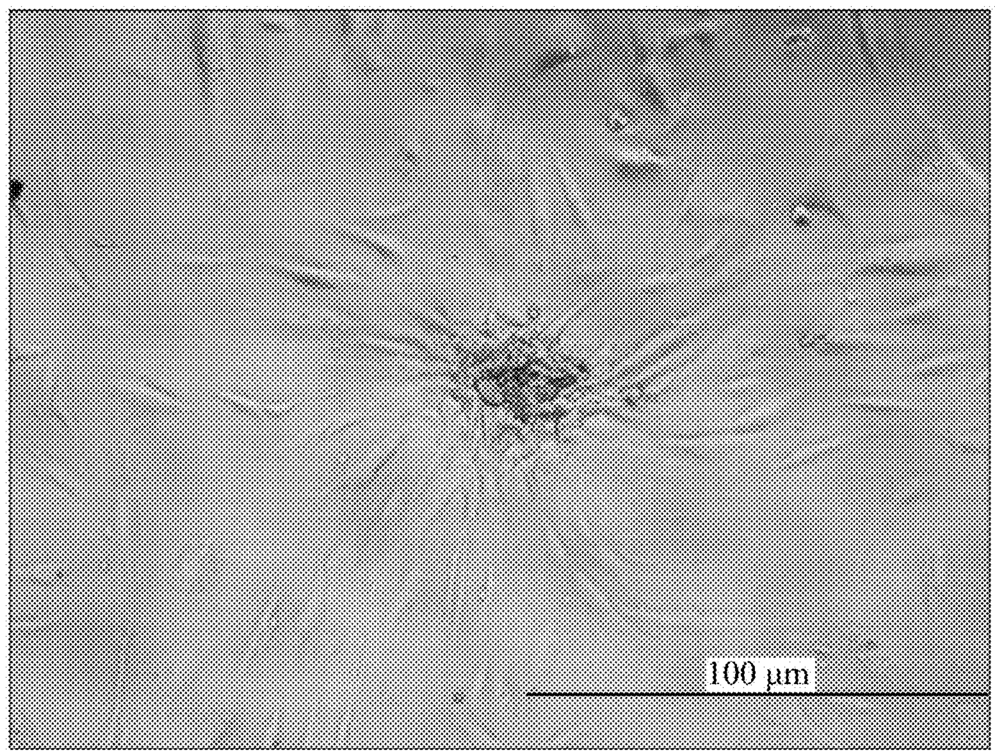
FIG. 6 is a photograph when the cell population of FIG. 5 was cultured in ReproStem medium for further one week.

FIG. 6 is a photograph showing the cells obtained by culturing the cell population of FIG. 5 in ReproStem medium (ReproCELL Inc.) for additional one week. As shown in the center of the photograph, a round Muse cell-like cell was observed.

Figure 7:
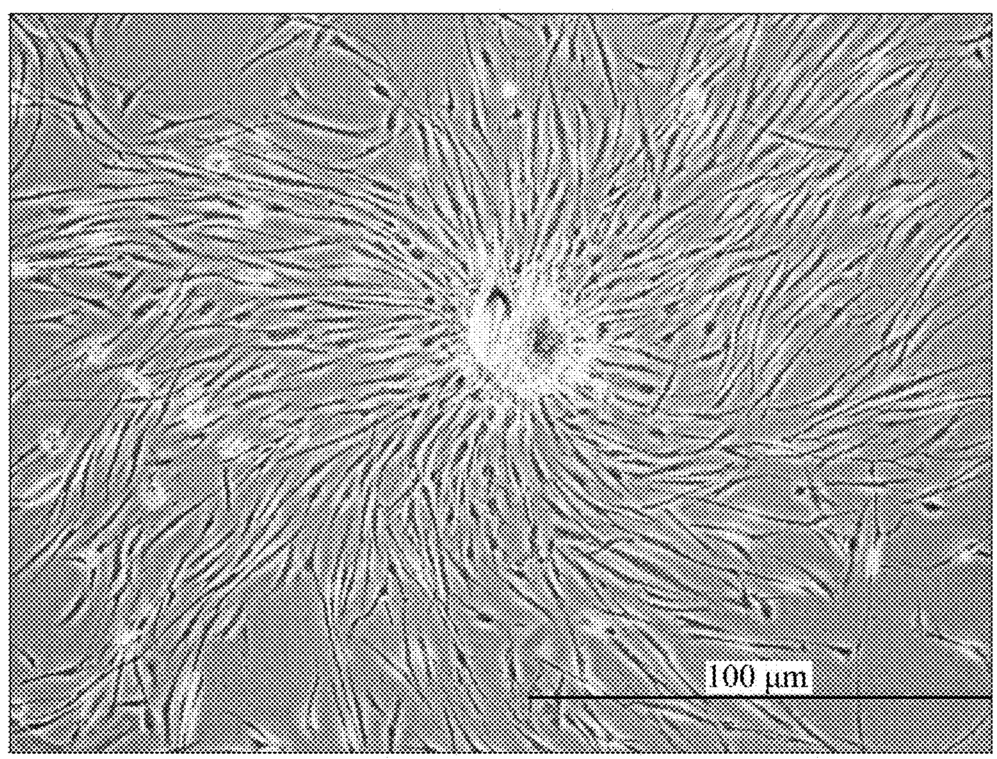
FIG. 7 is a photograph when the Muse cell-like cell of FIG. 6 was cultured in the ReproStem medium for further four days.

FIG. 7 is a photograph showing the cells obtained by culturing the Muse cell-like cell of FIG. 6 in ReproStem medium for additional four days. It was found that many juvenile fibroblasts were produced from the Muse cell-like cell at the center of the photograph and spread radially one after another. In addition, this Muse cell-like cell is shaped like an eyeball (with black and white portions).

Further, this Muse cell-like cell still survived at a time point after 18 weeks of culturing and continued producing fibroblasts. When currently commercially available fibroblasts are simply cultured, the fibroblasts undergo cellular senescence after about one month. In view of the above, it is surprising that the above cell survived for 18 weeks.

Figure 8:
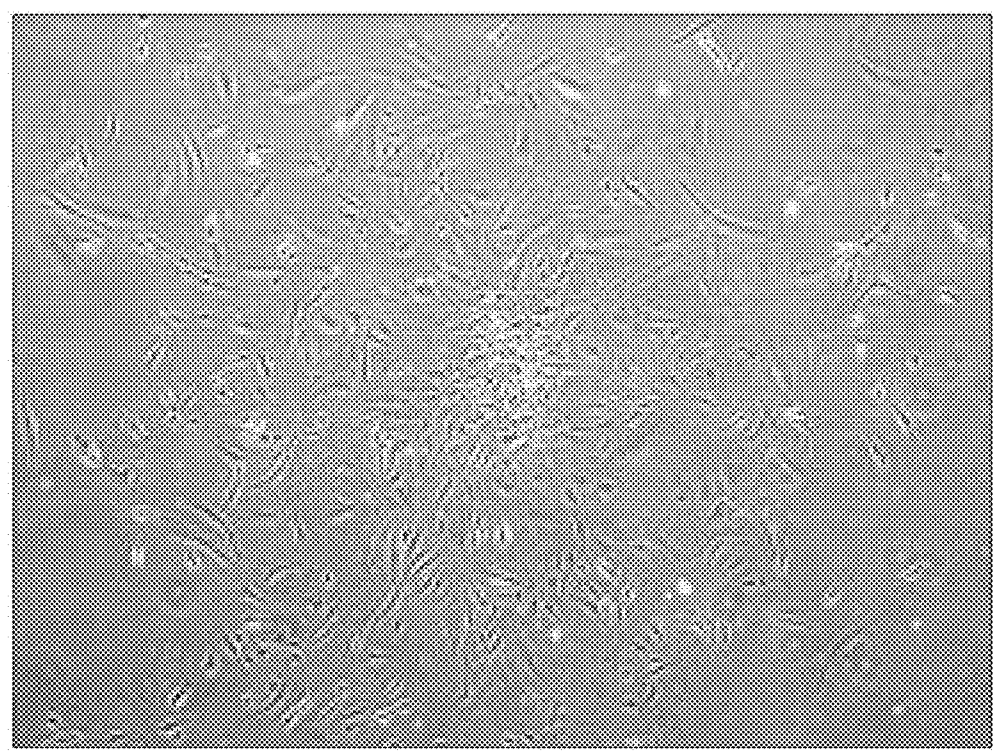
FIG. 8 is a photograph when the cell population of FIG. 5 was cultured in FBM+FGM-2 medium for further one week.

FIG. 8 is a photograph showing the cells obtained by culturing the cell population of FIG. 5 in FBM+FGM-2 medium (Ronza Inc.) for additional one week. In this case, no Muse cell-like cell was observed.

Figure 9:
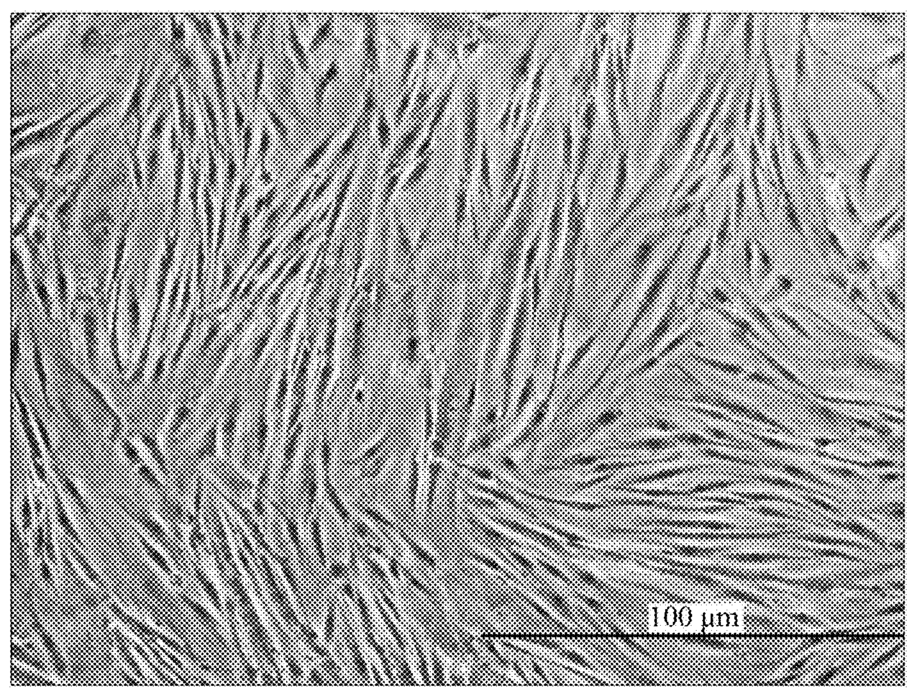
FIG. 9 is a photograph when the cell population of FIG. 8 was cultured in the FBM+FGM-2 medium for further four days.

FIG. 9 is a photograph showing the cells obtained by culturing the cell population of FIG. 8 in FBM+FGM-2 medium for additional four days. The fibroblasts each had a sharp outline and were more juvenile, healthy cells.

(2) Evaluation of Expression of Genes (2-1) Evaluation of Expression of CD105

Subsequently, the cells were detached using trypsin-EDTA (Gibco, Inc.) and RNA was extracted therefrom. Next, an RT-PCR (a OneStep RT-PCR kit, QIAGEN, Inc.) was used to measure the level of expression of CD105 (CD105 is a Muse cell marker). At this time, 25 ng of RNA was used for all the samples to normalize their Ct value, which was measured using a thermal cycler (LineGene, Bioflux, Inc.), to that of β-actin. Then, the level of expression of CD105 was calculated in accordance with the $2^{-\Delta\Delta}$ method.

Figure 10:
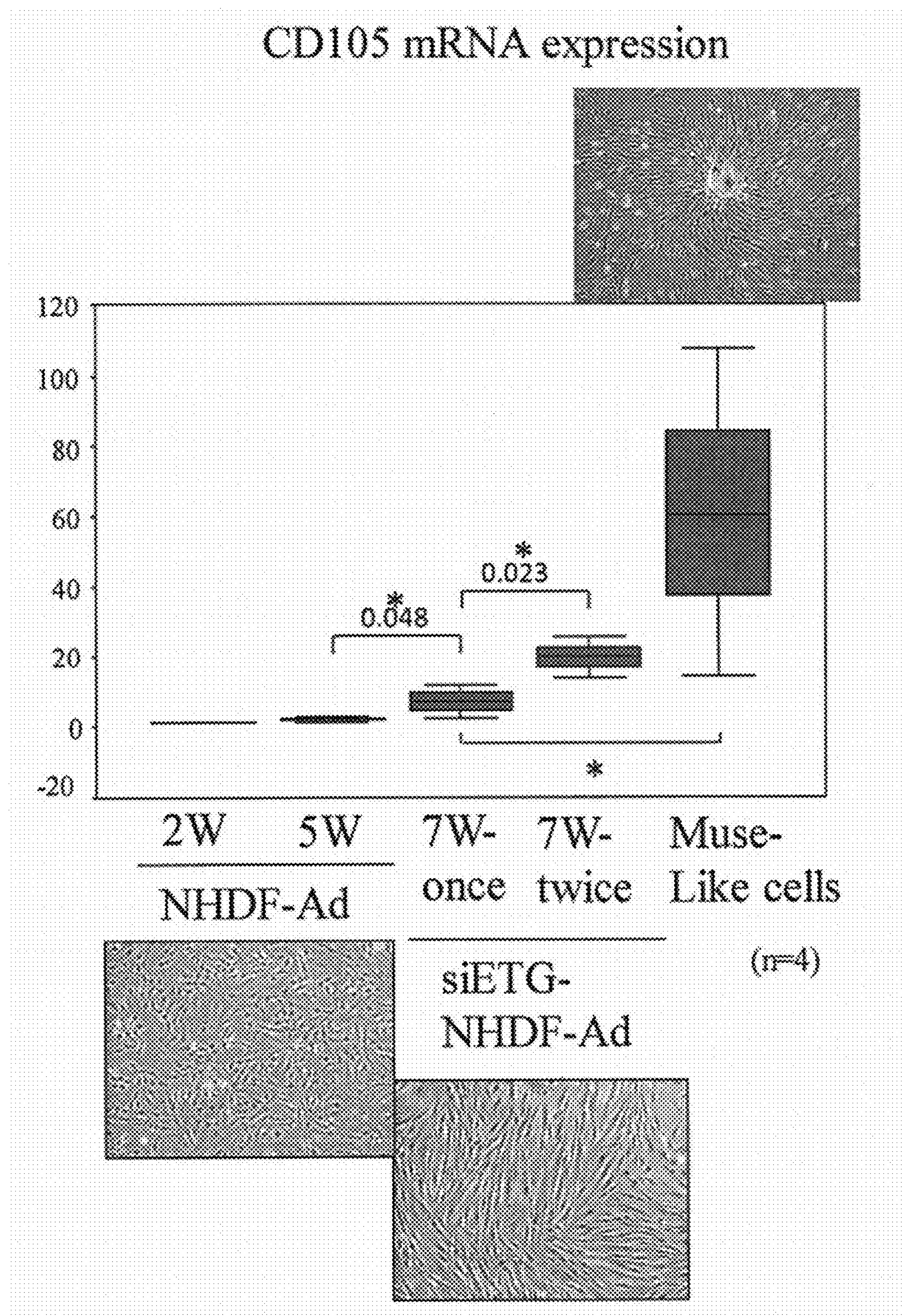
FIG. 10 shows the results of measuring the levels of expression of CD105 mRNA in cells with or without introduction of siETG.
Figure 11:
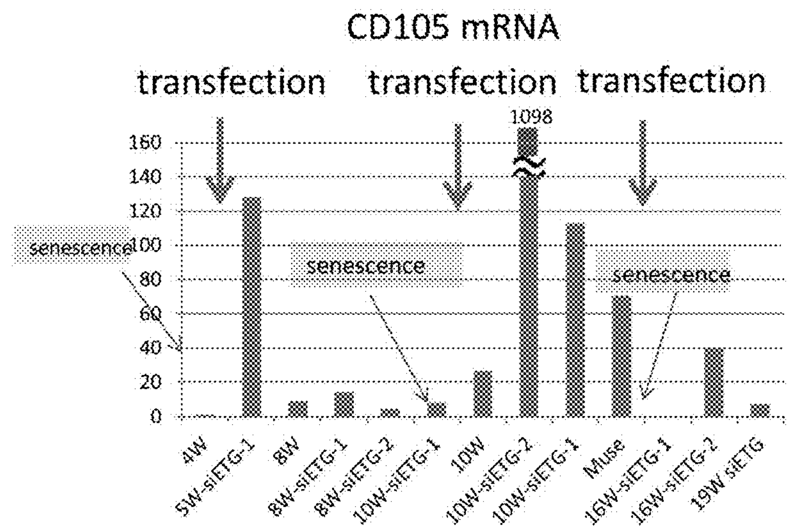
FIG. 11 illustrates the results of measuring the levels of expression of CD105 mRNA over time.
Figure 12:
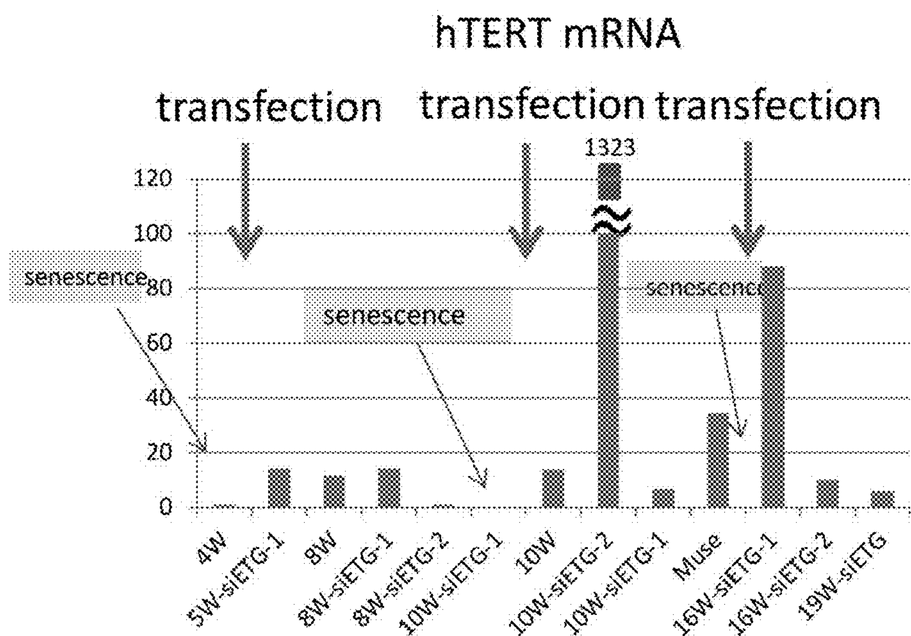
FIG. 12 illustrates the results of measuring the levels of expression of hTERT mRNA over time.
Figure 13:
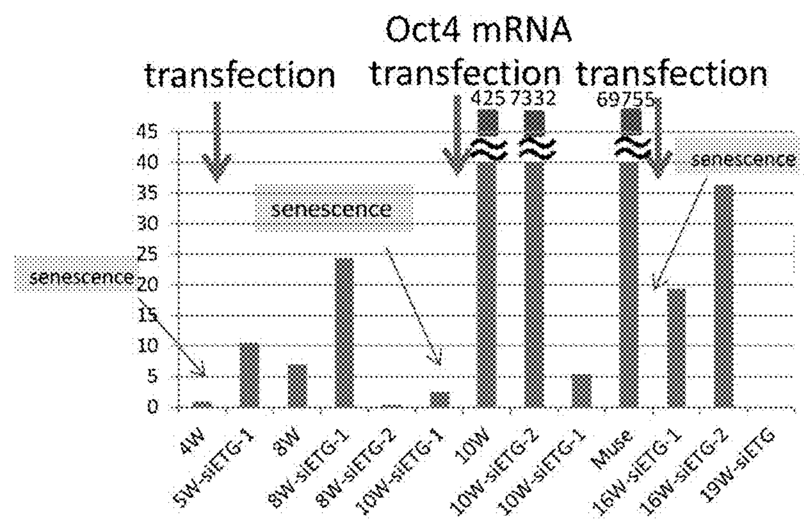
FIG. 13 illustrates the results of measuring the levels of expression of Oct4 mRNA over time.
Figure 14:
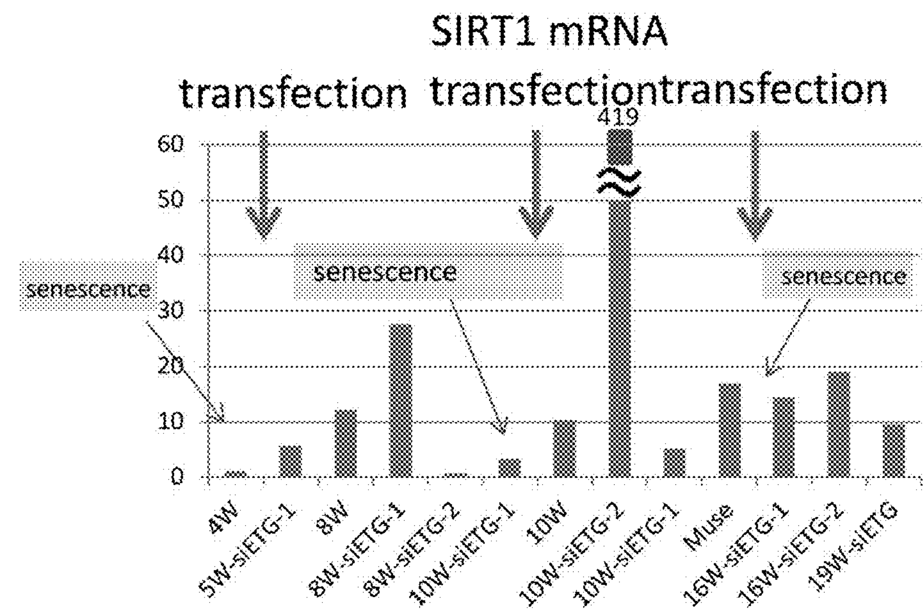
FIG. 14 illustrates the results of measuring the levels of expression of SIRT1 mRNA over time.
Figure 15:
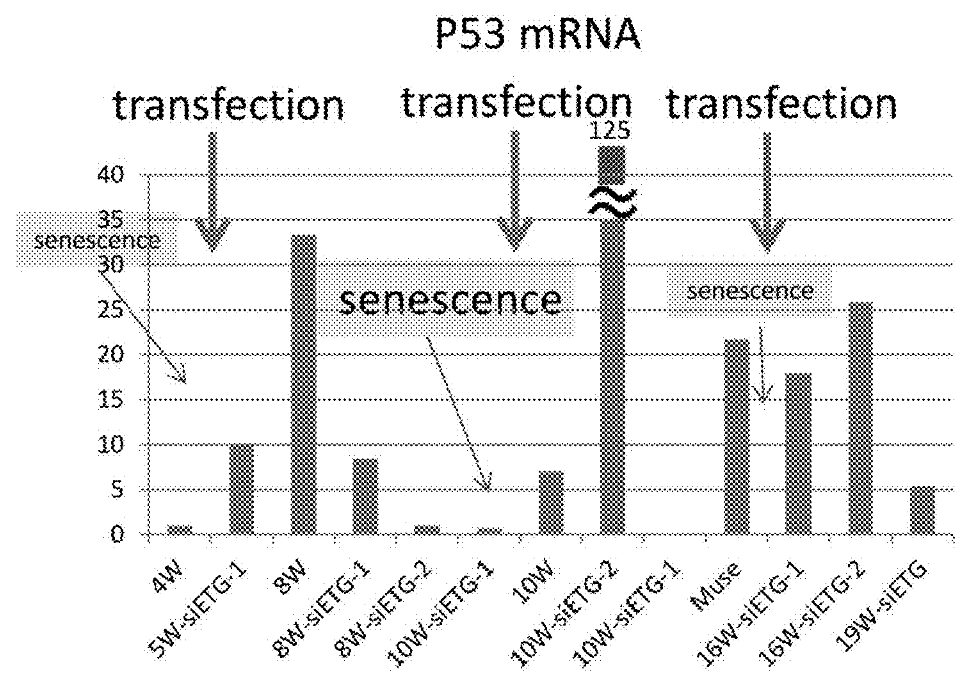
FIG. 15 illustrates the results of measuring the levels of expression of p53 mRNA over time.
Figure 16:
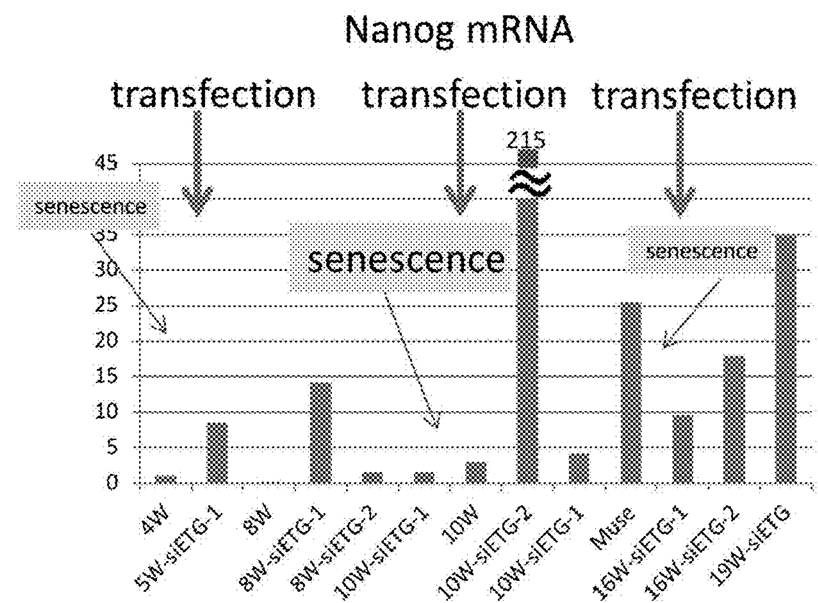
FIG. 16 illustrates the results of measuring the levels of expression of Nanog mRNA over time.

FIG. 10 shows the results. The NHDF-Ad into which no siETG (ELAVL2 siRNA, TEAD1 siRNA, and GATAD2B siRNA) were introduced had no expression of CD105 mRNA (see 2W and 5W of FIG. 10). By contrast, when siETG was introduced, there was expression of CD105 mRNA (see 7W of FIG. 10). Further, when a Muse cell-like cell was formed, there was a markedly high level of expression of CD105 mRNA (see the right end of FIG. 10).

(2-2) Evaluation of Expression of Each Gene

Subsequently, the cells were detached using trypsin-EDTA and RNA was extracted therefrom. Next, an RT-PCR was used to measure the level of expression of each gene. At this time, 25 ng of RNA was used for all the samples to normalize the Ct value, which was measured using a thermal cycler (LineGene, Bioflux, Inc.), to that of β-actin. Then, the level of expression of each gene was calculated in accordance with the $2^{-\Delta\Delta}$ method. When a graph was prepared, the level detected when the NHDF-Ad was cultured for 4 weeks was set to 1 and each level was represented as a fold change. Note that the cells under a condition in which the senescence has been induced or the cells just before cell death were infected with siETG-encoding viruses at MOI of 1 and the subsequent changes were likewise examined.

As a result, the Muse cell-like cell of this Example had high levels of expression of CD105, hTERT, Oct4, SIRT1, P53, and Nanog mRNAs. FIGS. 10 to 16 show the measured results. CD105 is a marker for a Muse cell. The hTERT and SIRT1 genes are expressed at high levels in juvenile cells. Oct4 and Nanog are markers for pluripotency. Also, p53 is one of malignant tumor suppressor genes.

The Muse cell-like cell of this Example had high levels of expression of not only CD105, but also SIRT1, hTERT, P53, Oct4, and Nanog in a synchronous manner. That is, the Muse cell-like cell as obtained in this Example was a pluripotent, juvenile, normal cell. In addition, because of the high levels of expression of p53 mRNA, the Muse cell-like cell of this Example can be said to have a low risk of developing a malignant tumor.

The letter "W" of the sample names in the Figures means a period (weeks) of culturing. The word "siETG" of the sample names in the Figures means a sample into which siETG was introduced. The signs "−1" and "−2" of the sample names in the Figures mean that there were two samples tested. The word "transfection" in the Figures means that siETG was introduced. The word "senescence" in the Figures means that cells underwent normal cell death. The name "10W-siETG-1" under the 9th bar from the left in the Figures is used to show the results as obtained by: reintroducing siETG into the cells represented by the name "10W-siETG-1" under the 6th bar; culturing the cells for 3 days; collecting them; and then performing measurements. The name "10W-siETG-2" under the 8th bar from the left in the Figures is used to show the results as obtained by: reintroducing siETG into the cells that are represented by the name "8W-siETG-2" under the 5th bar and were cultured for additional 2 months; culturing the cells for 3 days; collecting them; and then measuring the level of expression of each mRNA. The name "Muse" under the 10th bar from the left in the Figures is used to show the results as obtained by selecting and picking up one of the Muse cell-like cell-containing colonies observed after the cells represented by the name "10W-siETG-2" under the 8th bar from the left were cultured for 1 week and then by measuring the level of expression of each mRNA. The name "19W-siETG" in the Figures is used to show the results as obtained by culturing, for additional 3 weeks, the cells represented by the name "16W-siETG-2" under the 12th bar from the left.

Note that according to a time lapse movie independent of the above experiments, all the gene-introduced cells were changed at least temporarily into Muse cell-like cells. This is consistent with the fact that all the gene-introduced cells measured were positive for CD105. In addition, once the siRNA was introduced, the resulting NHDF-Ad was positive for CD105 regardless of their morphology and was then transformed into a Muse cell-like cell. When the cells were under stress (e.g., under a condition in which the cells were split sparsely after medium change), it was observed that the cells had an eyeball-like appearance. Some Muse cell-like cells were floating, and others were adherent. Phenomena that the adherent Muse cell-like cell produced new fibroblasts were observed. In addition, the fibroblasts sometimes appeared from nowhere.

(3) Collagen Productivity

Figure 17:
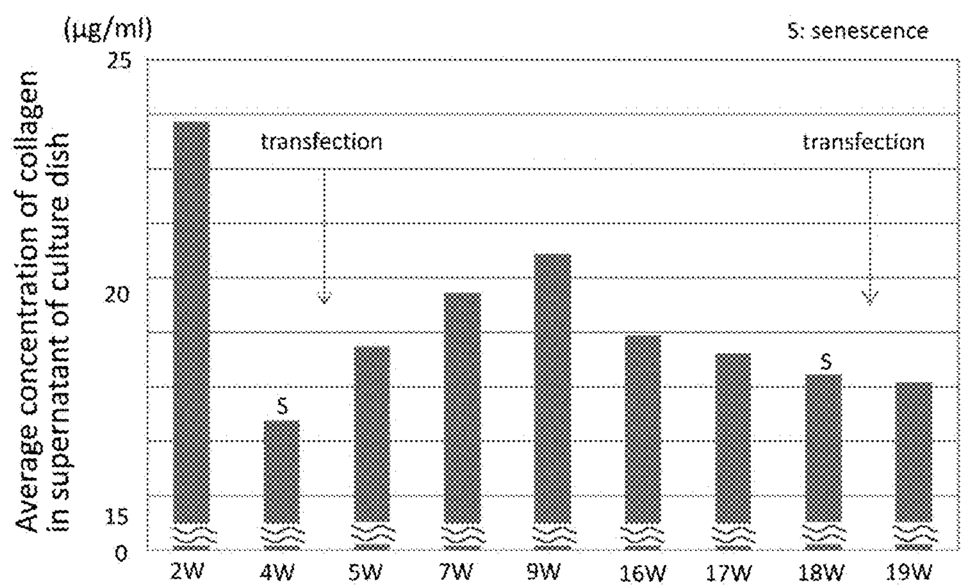
FIG. 17 illustrates the results in which the collagen productivity was measured over time.

The collagen productivity of the transformed cells was measured. A human collagen type I ELISA kit (ACEL, Inc.) was used for this measurement. After the gene introduction, the resulting fibroblasts were activated, thereby producing more amount of collagen (FIG. 17). Note that this graph represents one example. Because the senescence was induced after about six weeks, the genes were then introduced. Consequently, there was a group of the activated cells.

Example 2

Figure 18:
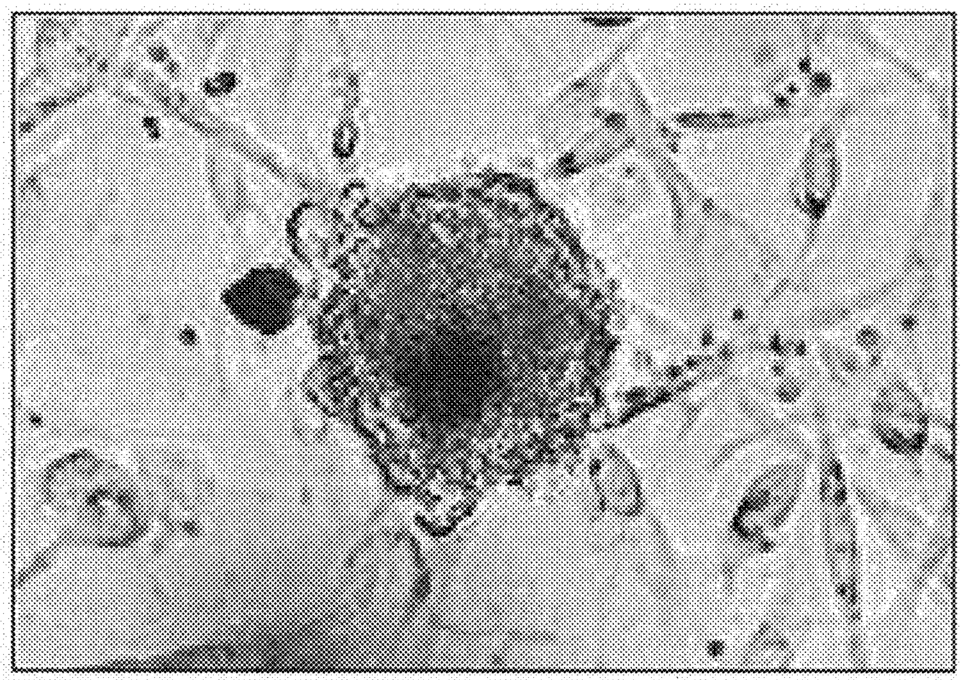
FIG. 18 is a photograph showing 293FT cells after hsa-miR-520d-5p was introduced.

Here, hsa-miR-520d-5p (SEQ ID NO: 32) was introduced into 293FT cells, and their cell morphology was observed. Specifically, first, the pMIR-520d-5p/GFP purchased from S&B, Inc., was used to construct a plasmid DNA. Next, the plasmid DNA was introduced into 293FT cells in substantially the same procedure as in the above. Then, the resulting virus particles were collected. After the titer was measured, TIG-1-20 cells were infected with the viruses. As a result, a Muse cell-like cell was observed (FIG. 18). Further, this Muse cell was cultured. Then, the Muse cell grew on the radially spread TIG-1-20 cells. In this regard, however, the cell was larger than the case of Example 1. Also, the cell outline was not sharp. That is, the cellular aging was in progress when compared with that of Example 1.

Hereinabove, the present invention has been described based on the Examples. These Examples are absolutely examples. It should be understood by those skilled in the art that various modifications are allowed, and those modifications are also within the scope of the present invention.

The invention claimed is:

1. A process for producing a Muse cell-like cell, comprising the step of introducing into a fibroblast cell or a fibroblast cell population: (a) an siRNA or shRNA specifically targeted to TEAD1 or a vector that encodes an siRNA or shRNA specifically targeted to TEAD1, (b) an siRNA or shRNA specifically targeted to ELAVL2 or a vector that encodes an siRNA or shRNA specifically targeted to ELAVL2, and (c) an siRNA or shRNA specifically targeted to GATAD2B or a vector that encodes an siRNA or shRNA specifically targeted to GATAD2B.

2. The production process according to claim 1, further comprising the steps of culturing the fibroblast cell or fibroblast cell population into which the siRNAs or shRNAs, or vectors encoding the same, have been introduced to generate a cultured cell population, and then collecting a Muse cell-like cell from the cultured a cell population.

3. The production process according to claim 1, wherein the Muse cell-like cell is positive for CD105.

4. The production process according to claim 1, wherein the Muse cell-like cell has a diameter of 5 μm or more.

5. A method for extending cellular or cell population replicative life span, comprising the step of introducing into a fibroblast cell or a fibroblast cell population (a) an siRNA or shRNA specifically targeted to TEAD1 or a vector that encodes an siRNA or shRNA specifically targeted to TEAD1, (ii) an siRNA or shRNA specifically targeted to ELAVL2 or a vector that encodes an siRNA or shRNA specifically targeted to ELAVL2, and (iii) an siRNA or shRNA specifically targeted to GATAD2B or a vector that encodes an siRNA or shRNA specifically targeted to GATAD2B.

6. A process for producing a cell expressing a high level of CD105 mRNA, comprising the step of introducing into a fibroblast cell or a fibroblast cell population (a) an siRNA or shRNA specifically targeted to TEAD1 or a vector that encodes an siRNA or shRNA specifically targeted to TEAD1, (b) an siRNA or shRNA specifically targeted to ELAVL2 or a vector that encodes an siRNA or shRNA specifically targeted to ELAVL2, and (c) an siRNA or shRNA specifically targeted to GATAD2B or a vector that encodes an siRNA or shRNA specifically targeted to GATAD2B.

7. The method according to claim 5, further comprising the steps of culturing the fibroblast cell or fibroblast cell population into which the siRNAs or shRNAs, or vectors encoding the same, have been introduced to generate a cultured cell population, and then collecting a Muse cell-like cell from the cultured a cell population.

8. The production process according to claim 6, further comprising the steps of culturing the fibroblast cell or fibroblast cell population into which the siRNAs or shRNAs, or vectors encoding the same, have been introduced to generate a cultured cell population, and then collecting a cell expressing a high level of CD105 mRNA from the cultured cell population.

* * * * *